(12) United States Patent
Mizuguchi

(10) Patent No.: US 12,324,676 B2
(45) Date of Patent: Jun. 10, 2025

(54) SYSTEM, COMPUTER PROGRAM AND METHOD FOR DISPLAYING TMT TEST RESULT

(71) Applicant: MAXELL, LTD., Kyoto (JP)

(72) Inventor: Tomohiko Mizuguchi, Kyoto (JP)

(73) Assignee: MAXELL, LTD., Kyoto (JP)

( * ) Notice: Subject to any disclaimer, the term of this patent is extended or adjusted under 35 U.S.C. 154(b) by 726 days.

(21) Appl. No.: 17/630,402

(22) PCT Filed: Jul. 15, 2020

(86) PCT No.: PCT/JP2020/027491
§ 371 (c)(1),
(2) Date: Jan. 26, 2022

(87) PCT Pub. No.: WO2021/020128
PCT Pub. Date: Feb. 4, 2021

(65) Prior Publication Data
US 2022/0280099 A1    Sep. 8, 2022

(30) Foreign Application Priority Data
Jul. 26, 2019 (JP) .................. 2019-138117

(51) Int. Cl.
*A61B 5/00* (2006.01)
*G16H 50/20* (2018.01)
*G16H 50/30* (2018.01)

(52) U.S. Cl.
CPC .......... *A61B 5/4088* (2013.01); *G16H 50/20* (2018.01); *G16H 50/30* (2018.01)

(58) Field of Classification Search
CPC ............................. A61B 5/4088; G16H 50/30
See application file for complete search history.

(56) References Cited

U.S. PATENT DOCUMENTS 9,883,831 B1 *   2/2018   Stewart ................ A61B 5/4088
2014/0100486 A1  4/2014   Alberts
(Continued)

FOREIGN PATENT DOCUMENTS

| JP | 2015-500042 A | 1/2015 |
| JP | 2017-144252 A | 8/2017 |

OTHER PUBLICATIONS

Yoshida, Hiroshi 'Trail Making Test (Trail Making Test, TMT),' Hijiyama University Faculty of Contemporary Culture, Department of Social and Clinical Psychology, [Online] 2015, Internet: <https://maruhi.heteml.net/programs/tmt/tmt.html> w/Machine English Translation.
(Continued)

*Primary Examiner* — Eric F Winakur
(74) *Attorney, Agent, or Firm* — Rimon P.C.

(57) ABSTRACT

A system for displaying the results of TMT test can acquire time-dependent changes in the position of a contact part on a coordinate plane as time-series coordinate data on the basis of an electric detection signal from a sensor, acquire an elapsed time associated with movement of the contact part as time data from a timer on the basis of the detection signal from the sensor, calculate a test value relating to the movement of the contact part on the basis of the data, and generate and output a characteristic image indicating a time-dependent change in the test value.

33 Claims, 24 Drawing Sheets

(56) References Cited

U.S. PATENT DOCUMENTS

2018/0336791 A1* 11/2018 Delis ................. A61B 5/4088
2019/0205777 A1    7/2019 Vlaskamp et al.

OTHER PUBLICATIONS

Yoshida, Hiroshi 'Program,' Hijiyama University Faculty of Contemporary Culture, Department of Social and Clinical Psychology, column of "Trail making test (TMT, v.1.005)") [Online] 2015, Internet: <https://maruhi.heteml.net/programs/programs.html> w/Machine English Translation.

Mabuchi, Takuya et al., 'A writing pressure analysis method for evaluation of trail making test using smart device,' 2017 6th International Conference on Informatics, Electronics and Vision & 2017 7th International Symposium in Computational Medical and Health Technology (ICIEV-ISCMHT), IEEE, 2017, pp. 1-6, [Online] Internet: <URL:https://ieeexplore.ieee.org/document/8338607>.

International Search Report issued in corresponding International Application No. PCT/JP2020/027491, dated Sep. 1, 2020 w/English Translation.

Written Opinion issued in corresponding International Application No. PCT/JP2020/027491, dated Sep. 1, 2020 w/English Translation.

* cited by examiner

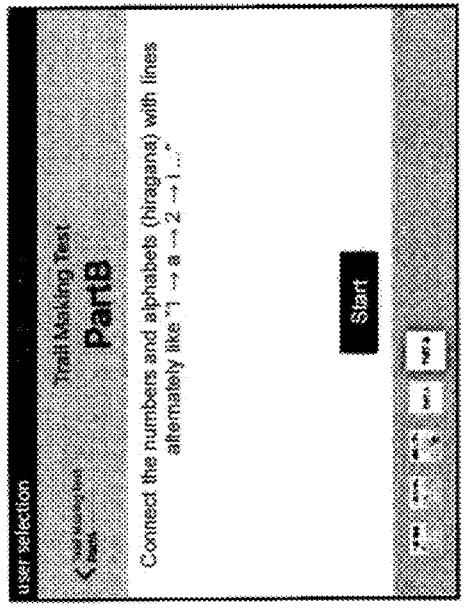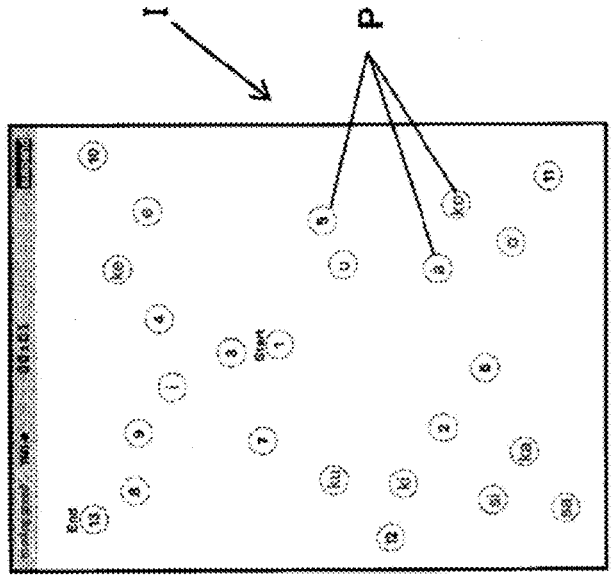
Fig. 3(b)
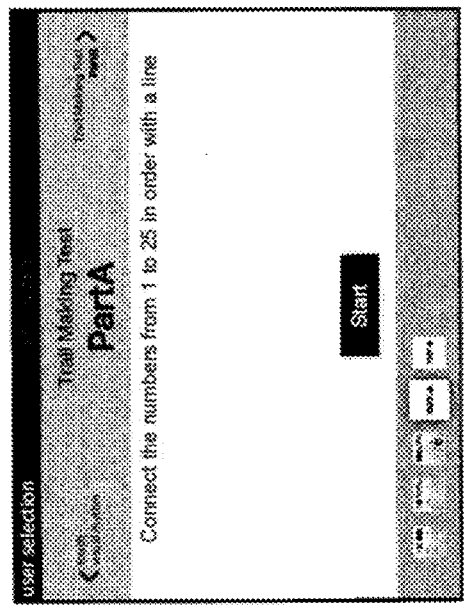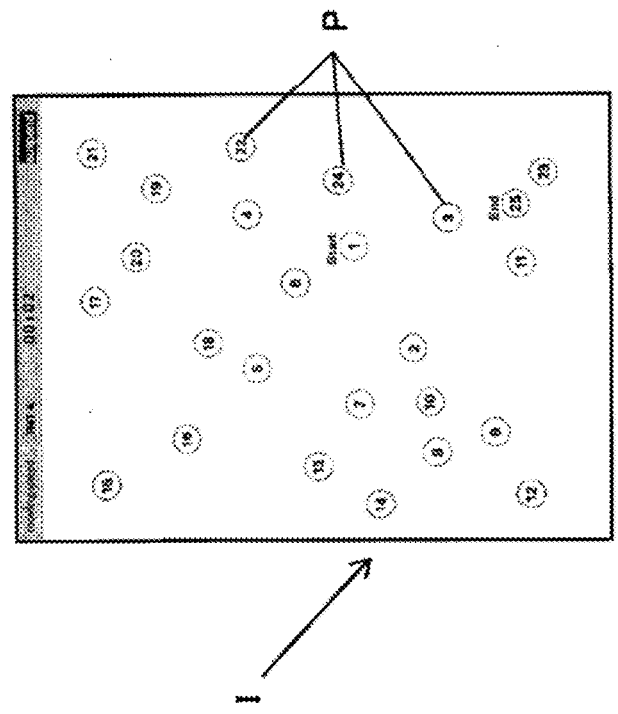
Fig. 3(a)

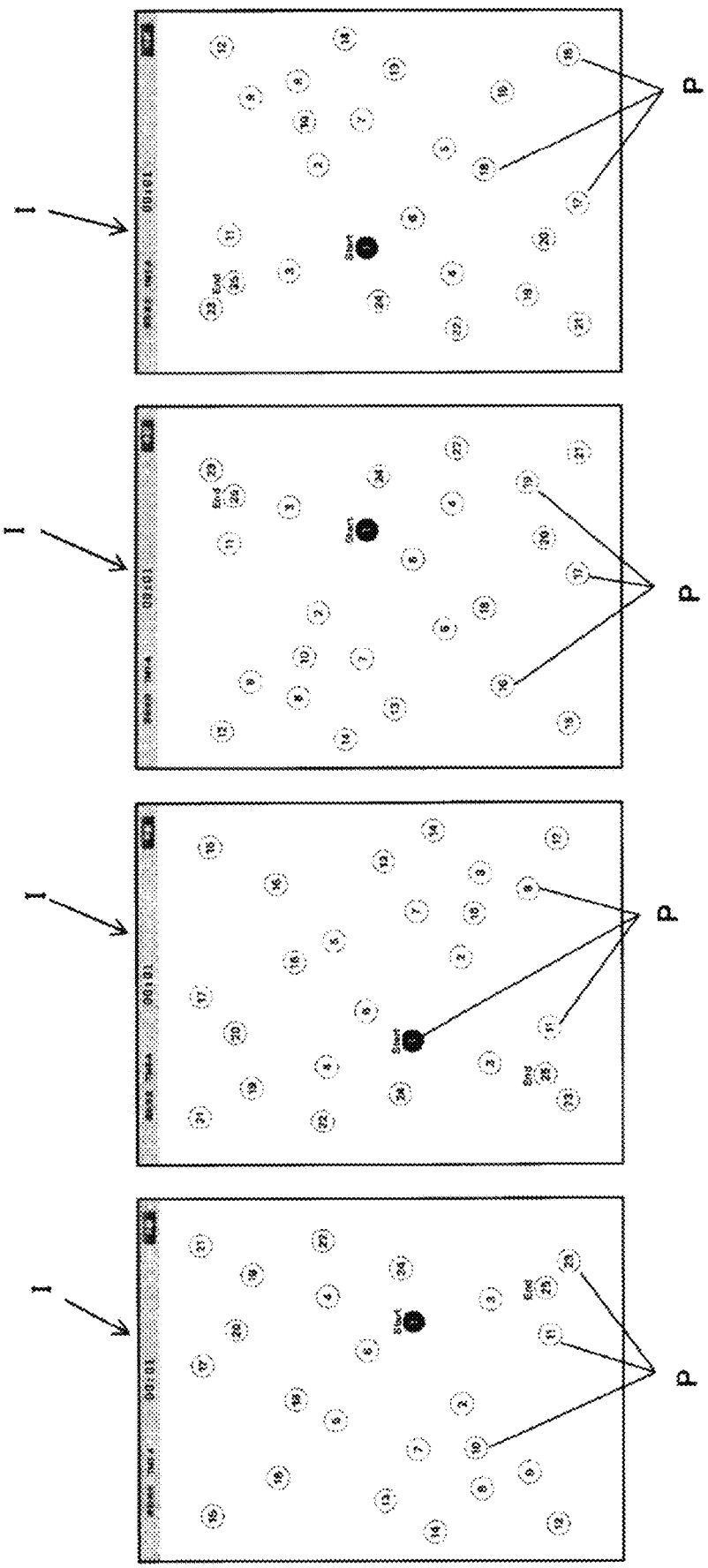

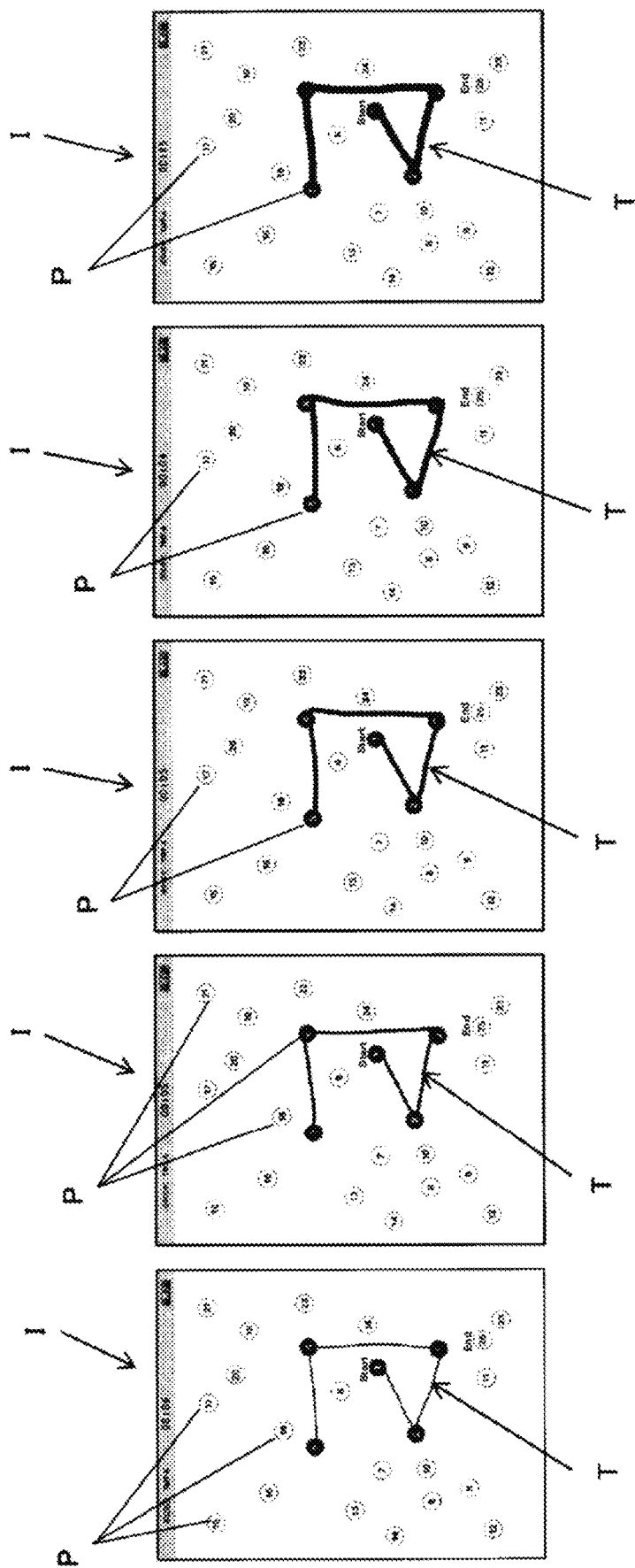

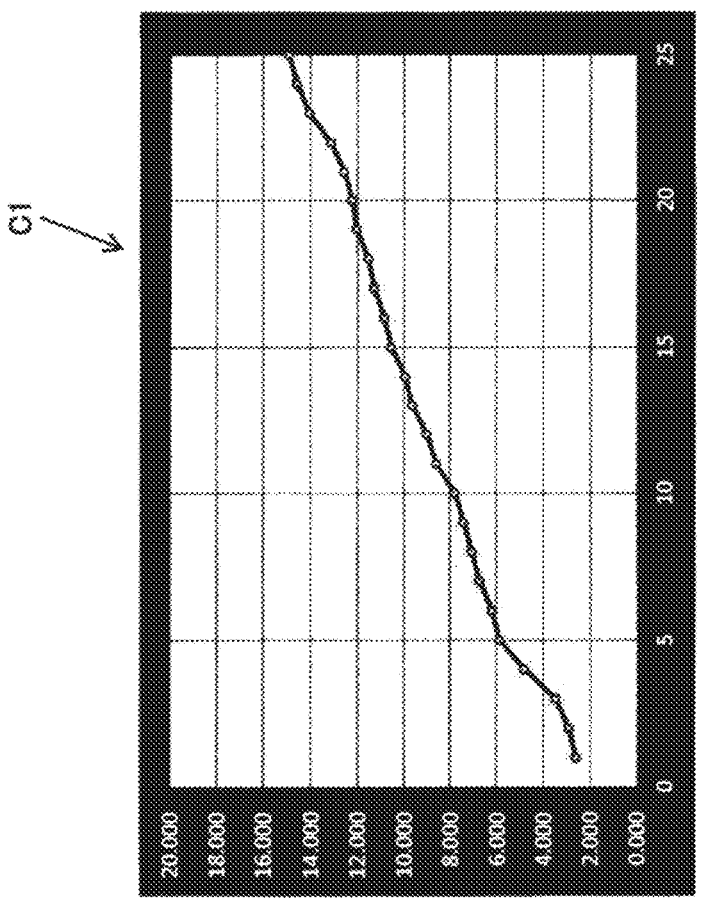
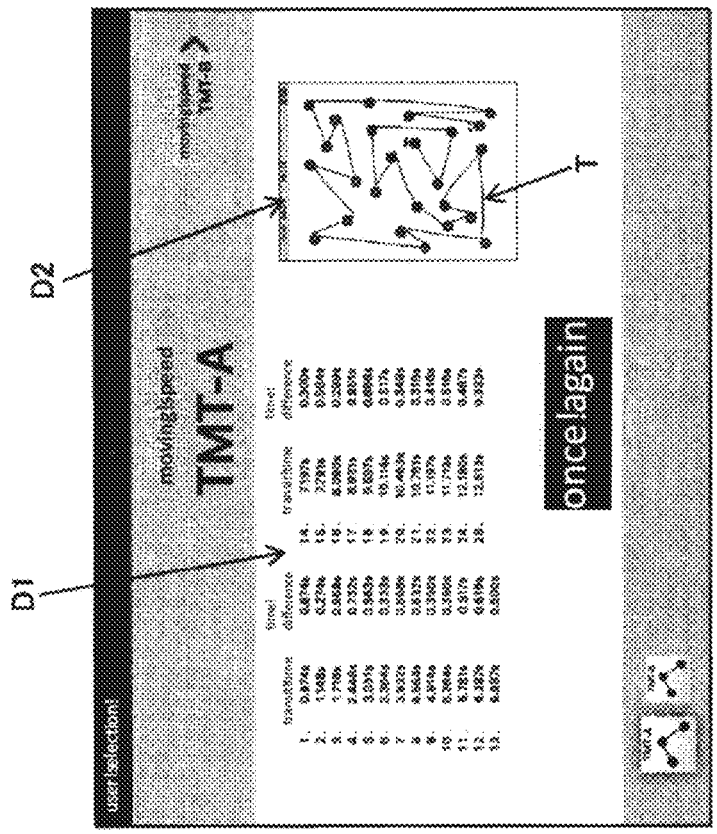
Fig.10(a)
Fig.10(b)

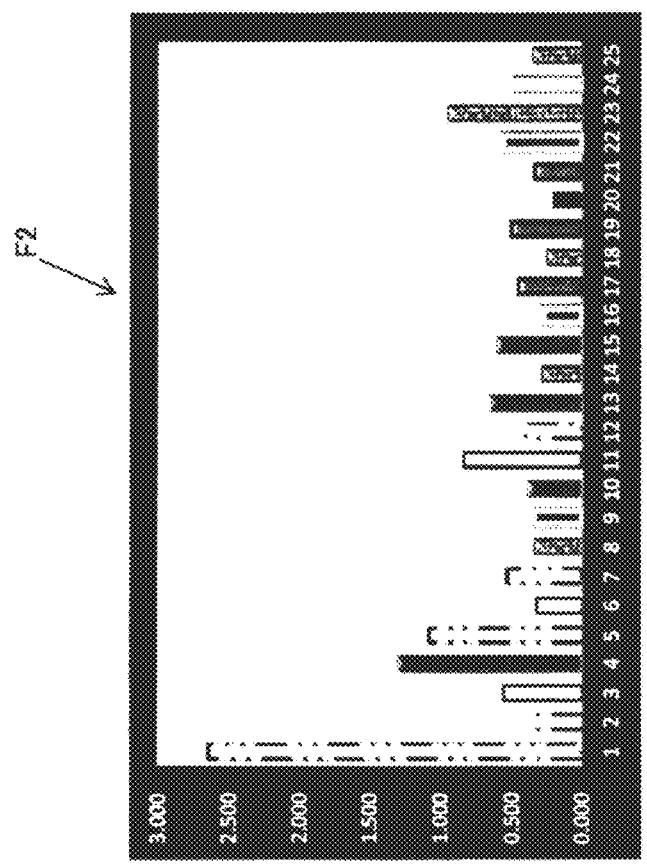
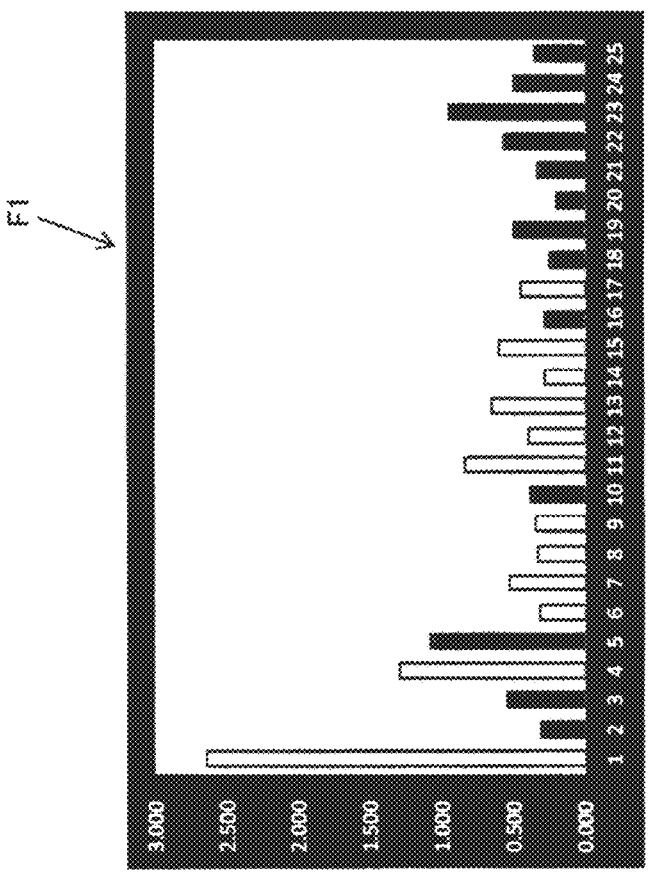
Fig.13(b)
Fig.13(a)

SYSTEM, COMPUTER PROGRAM AND METHOD FOR DISPLAYING TMT TEST RESULT

CROSS REFERENCE TO RELATED APPLICATIONS

This application is the U.S. National Phase under 35 U.S.C. § 371 of International Application No. PCT/JP2020/027491, filed on Jul. 15, 2020, which claims the benefit of Japanese Application No. 2019-138117, filed on Jul. 26, 2019, the entire contents of each are hereby incorporated by reference.

TECHNICAL FIELD

The present invention relates to a TMT test result display system, a computer program and a method capable of performing a TMT (Trail Making Test) test on a display and displaying the test result on the display.

BACKGROUND TECHNOLOGY

In recent years, with the aging society, dementia has become a serious concern. Usually, dementia is recognized as a disease in which symptoms progress with aging and it is difficult to clearly grasp an onset time. On the other hand, while it is difficult to recover from dementia when it actually develops and the symptoms progress, it is possible to prevent the onset by paying attention to normal lifestyle habits, or by taking appropriate measures at the early stages of onset, thus making it possible to delay the progress of the disease. Now, various screening tests that can detect the risk of dementia at an early stage have been proposed and implemented for an early detection and an early treatment of dementia.

As one of such screening tests, the Trail Making Test (hereinafter, simply referred to as TMT) is known (see, for example, Patent Document 1). This TMT is a test that uses lines to successively connect numbers and alphabets or hiragana randomly written on a paper, making it possible to perform a comprehensive measurement regarding a wide range of attention, working memory, spatial search, processing speed, perseveration, impulsivity, etc.

Specifically, the TMT test includes TMT-A test, TMT-B test and the like. In TMT-A test, a paper is used in which numbers from 1 to 25 are randomly arranged based on a predetermined rule. Then, a writing tool is used to form a connection from 1 to 25 with a line in an order until 25 is reached, followed by measuring a time necessary for reaching 25 which is an end. On the other hand, in TMT-B test, a paper is used in which 13 numbers from 1 to 13 and 12 alphabets from A to L or equivalent hiragana (a, i, u . . . , etc.) have been randomly arranged based on a predetermined rule. Then, a writing tool is used to form a connection in which numbers and alphabets (hiragana) are alternatively and successively connected using a line, followed by measuring a time necessary for arriving at an end.

Further, in such TMT tests, it is evaluated that the earlier the time required for those tests, the faster the processing speed will be and the longer the attention and spiritual concentration will continue. Besides, in TMT test, an actual test is always performed after undergoing an exercise corresponding to the test.

CITATION LIST

Patent Document

Patent Document 1: Japanese Unexamined Patent Application Publication No. 2017-144252.

SUMMARY OF THE INVENTION

Technical Problems

In the above-mentioned TMT test, it is necessary for an inspecting person such as a doctor or other responsible person to use a stopwatch or the like to measure a time required for the test. In addition, it is necessary to manually collect and analyze the test data including the measurement results. Moreover, since a trajectory drawn by a test subject moving a writing tool and tracing respective transit points such as numbers and alphabets in a predetermined order is managed on paper, it will be complex and difficult to perform an analysis of the information obtained from this process. Namely, in the conventional TMT test, it is troublesome to perform an operation from the execution of a test to the acquisition of the test result, resulting in an increased labor for the test.

In addition, regarding only the measurement value and the drawing trajectory obtained by manual measurement with a stopwatch and picture drawing by a test subject, there is a limitation to the cognitive function evaluation of the test subject, which is performed by exactly capturing various hidden information obtained in the test process.

Further, in the above-mentioned TMT test, it is necessary for the test subject to move the writing tool while keeping it in contact with the test paper so as not to allow it to float from the test paper, and it is also necessary to trace the transit points such as numbers and alphabets in a predetermined order. Besides, if the writing tool floats from the test paper, or if an order of transit route is incorrect, or a transit point is not surely passed, it is required that a caution be taken based on the judgment of the inspector. In this case, since an inspector judges (with a certain tolerance) an error during the progress of a test being performed on the test subject, the test data will vary depending on a difference in the tolerance of the judgment of the inspector, resulting in a situation where the test results may vary from test to test, depending on an inspector or each individual test.

The present invention has been accomplished in view of the above circumstances, and it is an object of the present invention to provide an improved TMT test result display system, as well as a computer program and a method therefor, all capable of quickly and easily performing a series of processes from test execution to test result acquisition, promoting the cognitive function evaluation of the test subject by exactly capturing various hidden information obtained in the test process, also capable of standardizing the test condition to prevent the test results from fluctuating, which will otherwise be caused due to different inspectors, thereby improving the reliability of the test result.

Solution to Problems

In order to solve the above-discussed problems, the present invention provides a TMT test result display system that enables TMT test on a display and displays test result on the display, the system comprising:

a test image generation circuit that electronically generates a TMT test image which is displayed on the display and is formed by setting transit points at multiple positions on a coordinate plane;

a test data acquisition circuit that allows a test subject to move a contact part in contact with the display surface of the TMT test image and to trace the transit points in a predetermined order, thereby acquiring time-dependent data of a drawing trajectory drawn by the test subject;

a data processing circuit that processes data acquired by the test data acquisition circuit so that the processing result can be displayed as the test result on the display; and a control circuit that controls the operations of each respective circuits wherein:

the test data acquisition circuit includes: i) a coordinate data acquisition circuit which, in accordance with a detection signal from a sensor that detects a contact of the contact part with the display surface of the TMT test image, acquires the coordinate data corresponding to the position of the contact part on the coordinate plane; ii) a time data acquisition circuit that uses a timer to acquire time data associated with the acquisition time of each coordinate data.

the data processing circuit includes: i) a arithmetic circuit that calculates a predetermined test value based on the coordinate data and the time data in the contact part; ii) an image generation circuit that generates a characteristic image which displays, in association with the position of transit point, a time-dependent change of the test value calculated by the arithmetic circuit; iii) an image output circuit that outputs a processed image including the characteristic image generated by the image generation circuit.

According to the TMT test result display system of the present invention having such a configuration, it is possible to perform the following operations. Namely, for example, when a test form for TMT test is selected and inputted from the mode selection menu displayed on the display, the test image generation circuit will generate TMT test image (for example, an image for TMT-A test, an image for TMT-B test, or the like) according to the selected test form (under the control of the control circuit) and display the image on the display. Then, when the test subject moves the contact part in contact with the display surface of the displayed TMT test image and traces the transit points in a predetermined order, the time-dependent data of the trajectory drawn thereby can be obtained by virtue of the test data acquisition circuit. The data acquired by the test data acquisition circuit is processed by the data processing circuit, and the processing result is dynamically and/statically displayed as test result on the display, by virtue of the data processing circuit in a selected display form. In fact, this is under the control of the control circuit and is performed by selecting and inputting a display form of the test result from the mode selection menu. As described above, according to the TMT test result display system of the present invention, a series of processes from the test execution to the test result acquisition (test result display) can be automated, so that it is not necessary for an inspector to use a stopwatch or the like to set the time required for the test. Further, there is no need to manually collect the test data containing the measurement values. Therefore, it is possible to quickly and easily perform a series of processes from the execution of the test to the acquisition of the test result (displaying the test result).

In addition to the above configuration, regarding the TMT test result display system of the present invention, the test data acquisition circuit includes: i) a coordinate data acquisition circuit that acquires coordinate data according to the position of the contact part on the coordinate plane, based on the detection signal from the sensor that detects the contact of the contact part with display surface of TMT test image, ii) a time data acquisition circuit that uses a timer to acquire time data associated with the acquisition time of each coordinate data. The data processing circuit includes: i) an arithmetic circuit that calculates a predetermined test value (for example, a test value related to the movement (or speed of movement) of the) in accordance with the coordinate data and the time data in the contact part; ii) an image generation circuit that generates a characteristic image which displays the time-dependent change of test value in association with the position of transit point; and iii) an image output circuit that outputs a processed image including the characteristic image generated by the image generation circuit. Namely, the TMT test result display system of the present invention can acquire a time-dependent change in the position of contact part on the coordinate plane (as time-series coordinate data) based on the electrical detection signal from the contact detection sensor, and can also acquire, as time data, an elapsed time associated with the movement of the contact part in accordance with the detection signal from the contact detection sensor. Meanwhile, based on the above data, it is possible to calculate a contact pressure with respect to the display surface of the TMT test image, which may be affected by test values such as the speed of movement of the contact part, acceleration, jerk degree, the transit time of transit point by the contact part, the time required between the transit points, and the movement speed, thereby making it possible to generate and output a characteristic image showing a time-dependent change of the test value. Therefore, it is possible to exactly capture various hidden information in the test process which otherwise cannot be obtained only by the measured values and drawing trajectories associated with manual measurement using a stopwatch or the like and picture drawing by the test subject, and to use the information in cognitive function evaluation of the test subject which is performed by a doctor or the like. In addition, according to the automatic test form accompanied by such electrical processing, it is possible to eliminate human measurement errors and standardize the test conditions, so that it is possible to prevent a situation in which the test results fluctuate with respect to each respective tests, thereby making it possible to improve the reliability of the test result.

Moreover, in the TMT test result display system of the present invention, the characteristic image generated by the image generation circuit displays a time-dependent change of the test value in association with the position of transit point. Therefore, it is possible to enable a detailed cognitive function evaluation by a doctor for each transit point zone, thereby providing a useful display form that assists cognitive function evaluation.

In addition, according to such an automated TMT test result display system, the test subject can perform the test by himself/herself without an inspector and can confirm the result on the spot.

In the above configuration, the "contact part" may be any device provided that it can be moved in contact with the display surface of the TMT test image to draw a drawing locus, and it can be an electronic input device such as a stylus pen operated by a test subject. In addition, it is also possible for the contact part to cover a broad concept that includes the finger of the test subject's own hand. Further, in the above configuration, the "sensor" may have any detection principle as long as it can detect the contact position of the contact part with respect to the display surface of the TMT test image, and is provided on the contact part side. Alternatively, a sensor may be provided on the display surface side. Further, the various circuits described above whose operation is controlled by a control circuit may be physically provided individually, but it is also possible to configure a functional part (or device) that integrates at least apart or all of these circuits (they may be electronically packed into one package). An important point is that such circuit may exist in any form as long as the functionality of each of these circuits is ensured.

Further, in the above configuration of the present invention, the image generation circuit divides the coordinate plane into a plurality of regions determined based on the input signal (input signal from the mode selection menu described above), and it is preferable to include an identification image generation circuit that generates characteristic images in a display form in which data corresponding to each respective regions can be visually distinguished from each other.

Here, the "visually identifiable display form" is a display form that enables the data corresponding to each area to be visually distinguished from each other by, for example, differences in color, line type, pattern, and the like. Further, the area division can be selected by a system user including an inspector and a test subject from, for example, the mode selection menu described above, and the control circuit controls the image generation circuit based on the input signal from the mode selection menu accompanying the selection, thereby generating the identification display image.

According to such an identification display function, for example, the coordinate plane is divided into two left and right regions. Namely, the coordinate plane is divided into a right side region consisting of the first and fourth quadrants and a left side region consisting of the second and third quadrants. The data corresponding to the right side region and the left side region are color-coded by, for example, two colors. Alternatively, it is possible to set a plurality of (for example, 8) boundary lines extending radially from the coordinate origin and separated from each other at equal angular intervals around the coordinate origin, and a plurality of (for example, 8) regions in the coordinate plane defined by these boundary lines. If the data corresponding to each of these areas is color-coded by the number of colors corresponding to the number of areas (for example, 8 colors) and identifiably displayed, it is possible to grasp at a glance a tendency peculiar to the position and direction in the coordinate plane. For example, it is possible to grasp at a glance a tendency of the test result depending on whether the test subject's dominant hand is the left hand or the right hand, or the tendency of the test result caused due to the damaged part of the brain. For example, it is possible to clearly grasp at a glance a fact that the visual acuity of one eye is deteriorated, or it is possible to visually and clearly grasp the tendency of test results caused due to local or overall deterioration of physical function, and to facilitate the evaluation of the cognitive function of the test subject which is performed by a doctor or the like.

Further, in the above configuration of the present invention, it is preferable that the image generation circuit generates, as a processed image, a drawing locus reproduction image which dynamically and/or statically displays the drawing locus drawn by the contact part, in a predetermined zone of the transit point determined based on the input signal. According to such a configuration, a system user such as a doctor who evaluates a test result can cut out a part of a drawing trajectory and check it as a still image or a moving image (preferably as an enlarged display screen) as needed. For example, by reproducing and displaying a drawn portion of interest, it becomes possible to extract an abnormal drawing trend without any omission and use it for cognitive function evaluation. In this case, it is preferable to be able to select, from the mode selection menu displayed on the display, a transit point zone to be reproduced as a display form of the test result.

Further, in the above configuration of the present invention, the sensor further detects the contact pressure of the contact part with respect to the display surface of the TMT test image, and the test data acquisition circuit further includes a contact pressure data acquisition circuit that acquires contact pressure data corresponding to the position of the contact part on the coordinate plane in accordance with the detection signal from the sensor. The image generation circuit preferably generates a contact pressure image as a processed image, which displays a time-dependent change in contact pressure, in association with the position of a transit point. According to such a configuration, it is possible to detect a contact pressure (a pen pressure exerted on the display surface of the TMT test image through the contact part when the test subject draws a drawing locus) that can be an index for cognitive function evaluation, and to generate and output a contact pressure image related to the contact pressure. Therefore, it is possible to provide a useful display form that assists the evaluation of cognitive function. It is known that impaired cognitive function may result in poor control of pen pressure. As a result, such a contact pressure images can be of great help in cognitive function evaluation. Further, it is preferable to enable the above-mentioned visually identifiable display form to be applied to such a contact pressure image. In addition, since the contact pressure image displays a time-dependent change in association with the position of transit point, it is possible for the doctor to perform a detailed cognitive function evaluation for each transit point zone.

Further, the TMT test result display system having the above-described configuration further includes a transit detection circuit that detects the passing through the transit point by the contact part (based on the detection signal from the sensor), while the transit detection circuit includes a setting circuit for variably setting a range of the coordinate region in which it can be determined that the contact part has passed through the transit point.

Specifically, with such a configuration, for example, transit point is displayed as a circular region in the TMT test image, and is defined as a coordinate region inside a reference circle in which the range of coordinate region is a circular region where it is possible to determine that the contact part has passed through the transit point. Even under such a condition, the transit detection circuit can for example set a virtual circle having a radius X % larger than the radius of the reference circle (a circle surrounding the reference circle from the outside), so that it is possible to determine that the contact part has passed through the transit point even if the contact part has not passed through the inside of the reference circle (as long as it has passed through the inner side region of the virtual circle). At this time, it is possible for the setting circuit to change the value of X within the range of 0 to a predetermined value.

According to such a configuration, not only the passing through the transit point by the contact part can be detected through the cooperation between the sensor and the transit detection circuit, but also the setting circuit can make it possible to set an allowable range for determining whether the contact part has passed through the transit point. At this time, while it is possible to give a discretion to the transit judgment, it is also possible to impose certain restrictions on the discretion by defining a variable setting range using coordinates. Further, it is possible to perform a test with a degree of freedom according to an actual situation, while at the same minimizing a fluctuation of the test result caused due to the discretion.

Further, in the above configuration of the present invention, it is preferable that the image generation circuit displays a visual index indicating a threshold value as an evaluation standard of the TMT test result on the processed image. In this way, it becomes possible to grasp at a glance the quality of the test result by confirming the index, thereby ensuring a quick cognitive function evaluation. In this case, regarding the threshold value that serves as the evaluation standard for the TMT test result, it is possible to enumerate, for example, a value that can be a boundary value between good and bad of the test result, such as a speed value of movement, an acceleration value, a jerk value of the contact part, a time required for passing through the transit point by the contact part, a required time between transit points, and a contact pressure of the contact part with respect to the display surface of the TMT test image. Further, regarding the visual index displayed on the processed image, it is possible to enumerate lines, dots, and patterns. Further, it is preferable that the threshold value as an evaluation standard of the TMT test result can be set to an arbitrary value from the mode selection menu or the like, based on the accumulated past medical data or the like. In addition, it is preferable that the evaluation standard of the TMT test result can be set (for example, selection of the processed image in which the index should be displayed) from the mode selection menu or the like.

Further, it is preferable that the TMT test result display system having the above configuration further has a memory for storing test data including coordinate data and time data and a processed image generated by an image generation circuit. According to this configuration, data can be stored in the memory and necessary data can be read out in a timely manner as needed. Further, for example, it is possible to evaluate the course of symptoms by comparing the accumulated historical data with each other, or to make a final certification of the evaluation based on the data accumulated in the memory. Here, the "test data" means all the unprocessed data that can be acquired by the test data acquisition circuit.

Moreover, in the above configuration of the present invention, it is preferable that the image output display circuit outputs a processed image stored in a memory and determined based on an input signal, in a display form including an alternative or parallel display determined based on the input signal. In this way, it is possible to customize an image display form of test result, particularly by displaying the processed images in parallel, thereby making it possible to perform a comparison among several test results, thus realizing a display form useful for cognitive function evaluation.

Further, in the above configuration of the present invention, it is preferable that the image generation circuit generates a processed image using test data stored in a memory and determined based on an input signal. Therefore, instead of generating only a predetermined processed image based on predetermined test data, it is possible to use the mode selection menu to arbitrarily combine the test data stored in the memory, so as to generate a desired processed image (for example, an image other than the characteristic image that displays a time-dependent change of test value in the contact part, specifically, for example, a graph showing the relationship between contact pressure and acceleration), thus making it possible to customize not only a display form, but also a data processing.

Further, the present invention also provides a computer program and method for displaying the TMT test result, in addition to the above-mentioned TMT test result display system.

Effects of the Invention

According to the present invention, it is possible to provide an improved TMT test result display system, an improved computer program and an improved method therefor, which can quickly and easily perform a series of processes from test execution to test result acquisition, exactly catch various hidden information obtained in the test process, thus making it possible to use the information in evaluation of the cognitive function of a test subject, standardizing the test conditions, preventing the test results from being fluctuated due to different inspectors, thus improving the reliability of the test results.

DESCRIPTION OF THE DRAWINGS

FIG. 3(a) shows an example of a TMT test image for TMT-A test which is displayed on a display, and FIG. 3(b) shows an example of a TMT test image for TMT-B test which is displayed on a display.

FIG. 6(a) shows an example of a TMT test image when pattern A is selected on the display setting screen of FIG. 4, FIG. 6(b) shows an example of a TMT test image when pattern B is selected on the display setting screen of FIG. 4, FIG. 6(c) shows an example of a TMT test image when pattern C is selected on the display setting screen of FIG. 4, FIG. 6(d) shows an example of a TMT test image when pattern D is selected on the display setting screen of FIG. 4.

FIG. 7 is a display form in which the display line of a drawing locus drawn by a test subject on a display surface of a TMT test image is gradually thickened from one step to five steps, wherein FIG. 7(a) shows a drawing locus on the TMT test image when the line thickness is set at the first stage on the display setting screen of FIG. 4, FIG. 7(b) shows a drawing locus on the TMT test image when the line thickness is set at the second stage on the display setting screen of FIG. 4, FIG. 7(c) shows a drawing locus on the TMT test image when the line thickness is set at the third stage on the display setting screen of FIG. 4, FIG. 7(d) shows a drawing locus on the TMT test image when the line thickness is set at the fourth stage on the display setting screen of FIG. 4, FIG. 7(e) shows a drawing locus on the TMT test image when the line thickness is set at the fifth stage on the display setting screen of FIG. 4.

FIG. 10(a) shows an example of a processed image displayed as a test result on a display, and FIG. 10(b) shows an example of a characteristic image (a characteristic image in which a time-dependent change of the contact part's transiting time for passing through the transit point has been displayed in association with the position of transit point)

FIG. 13 is an example of a characteristic image displayed as a test result on a display (a characteristic image in which a time-dependent change of a time required by the contact part between transit points has been displayed in association with the position of the transit point). FIG. 13(a) shows an example of a display form in which the coordinate plane of the TMT test image is divided into two left and right regions, and the data corresponding to each of the regions are displayed so as to be visually distinguishable from each other. FIG. 13(b) shows an example of a display form in which the coordinate plane of the TMT test image is divided into eight regions in eight directions, and the data corresponding to each of these regions are visually distinguished from each other.

DESCRIPTION OF EMBODIMENTS

Hereinafter, embodiments of the present invention will be described with reference to the accompanying drawings.

Figure 24:
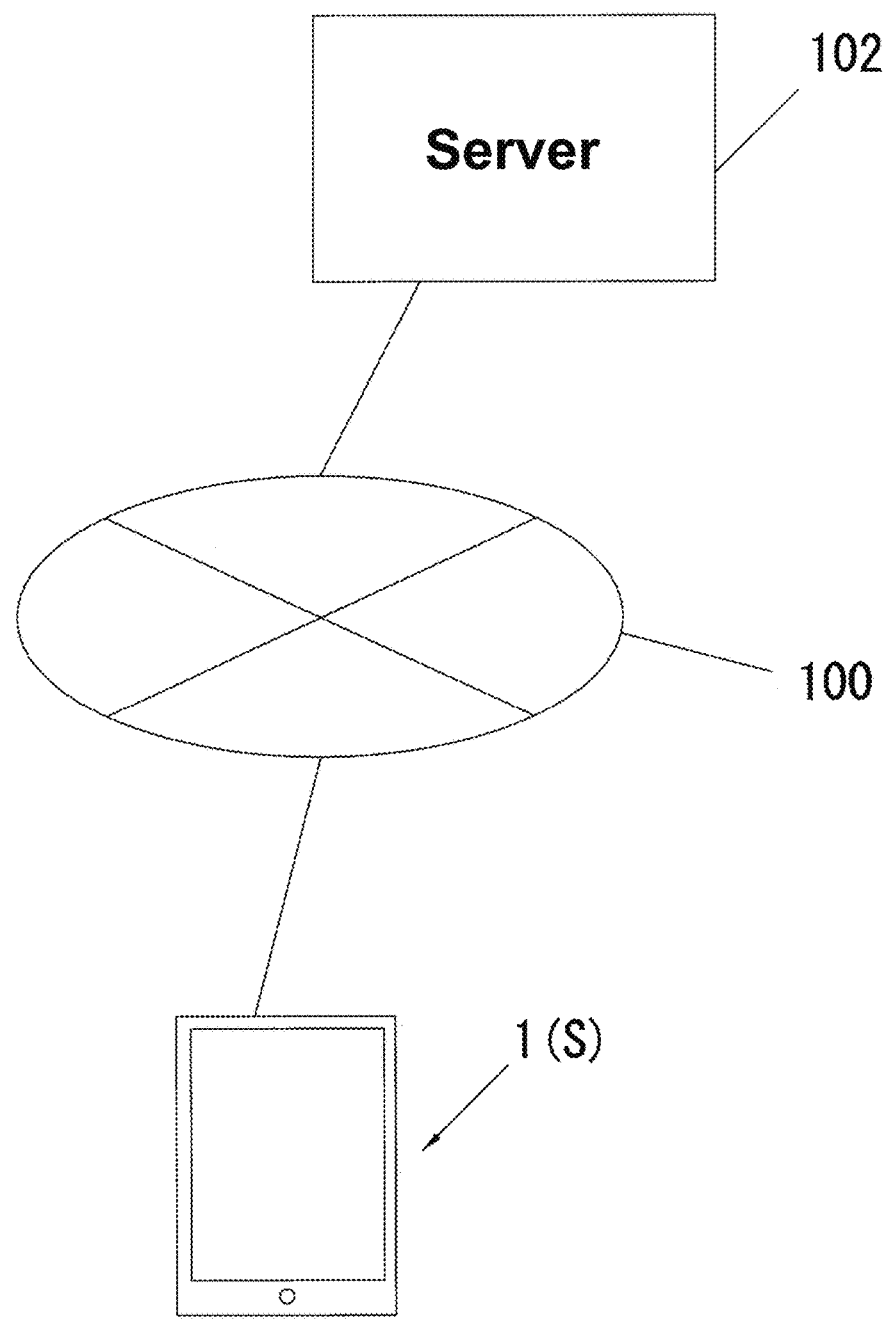
FIG. 24 is a conceptual diagram showing a state in which a terminal serving as a TMT test result display system according to an embodiment of the present invention is connected to a server via communication means.

The TMT test result display system that enables TMT test on a display and can display the test result on the display is configured as a terminal in the present embodiment. As shown in FIG. 24, although it is conceivable that such a terminal 1 (TMT test result display system S) may be connected to the server 102 via the communication means (network) 100 (this will be described later), it is possible to adopt any form for the system. On the other hand, in the present embodiment it is also possible for the display system to be configured as a tablet-type thin computer, but may also be a personal computer, a smartphone, or the like.

In the present embodiment, the terminal 1 itself is provided with a display so that the TMT test and the test result display can be performed by itself. On the other hand, it is also possible to form a system in which the TMT test and test result display may be performed in cooperation with a separate display. Alternatively, the TMT test result display system S may exist as a computer program that enables such a TMT test and display of the test result by a computer or a computer program product in which such a computer program is stored.

Figure 1:
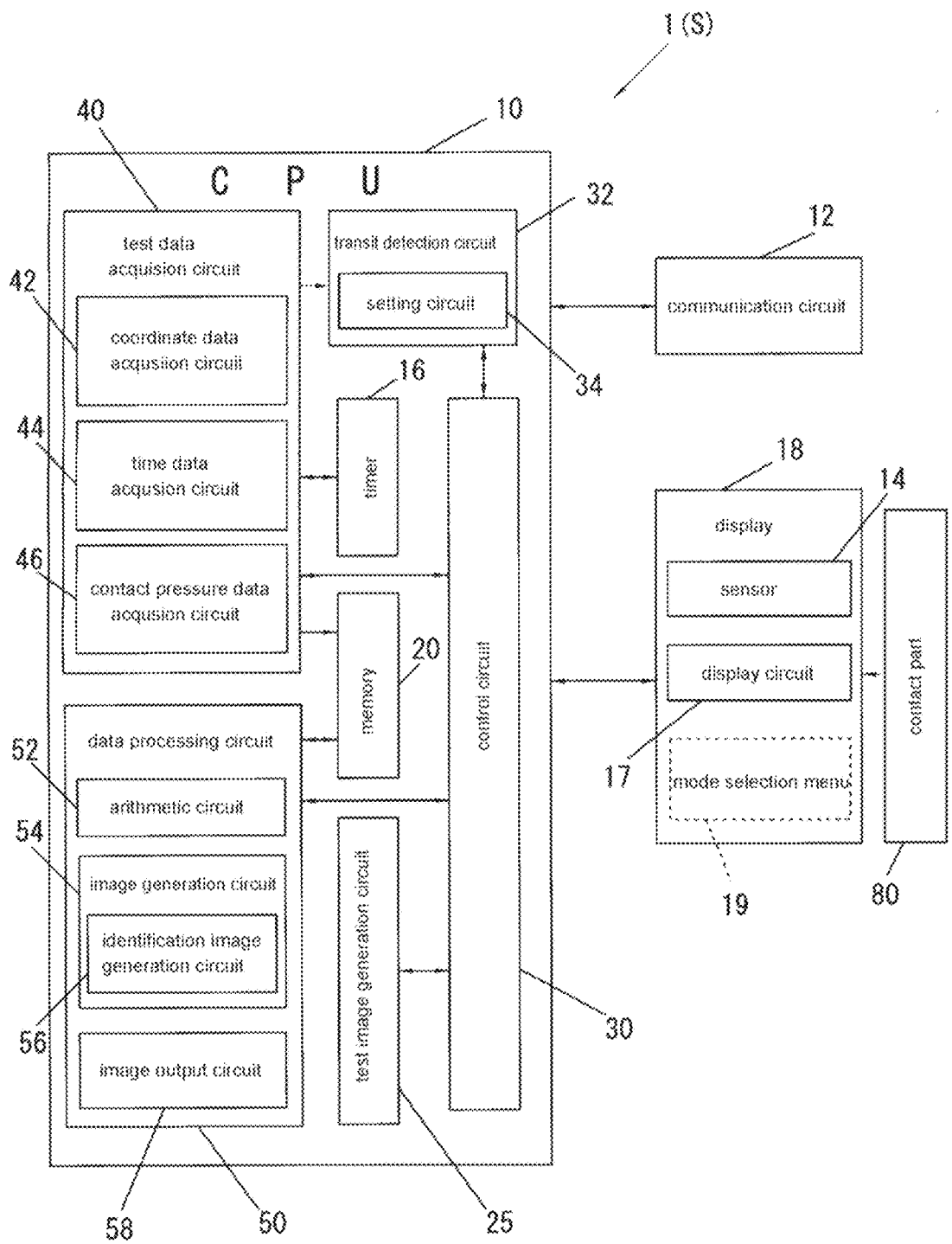
FIG. 1 is a block diagram showing a configuration of a TMT test result display system according to an embodiment of the present invention.

FIG. 1 shows a block diagram indicating the conceptual configuration of the terminal 1. As shown, the terminal 1 serving as the TMT test result display system S includes, for example, CPU 10 and a display 18 which is a liquid crystal display device. The CPU 10 includes: i) a test image generation circuit 25 that electronically generates TMT test image I which is displayed on the display 18 and is formed by setting predetermined transit points P (which will be described later with reference to FIG. 3 and subsequent figures) at a plurality of positions on the coordinate plane; ii) a test data acquisition circuit 40 which acquires time-dependent data of drawing trajectory drawn by the test subject moving contact part 80 in contact with the display surface of the TMT test image I, followed by tracing the transit points P in a predetermined order; iii) data processing circuit 50 that processes the data acquired by the test data acquisition circuit 40 so that the processing result can be displayed as the test result on the display 18; iv) a control circuit 30 that controls the operation of respective circuits 25, 40, 50 based on an input signal from the mode selection menu 19 displayed on the display 18 so that it is possible to select a test form of the TMT test and a display form of the test result. In the present embodiment, the control circuit 30 controls the display circuit 17 provided on the display 18 to display various images on the display 18.

In the present embodiment, the contact part 80 may be configured as an electronic input device such as a stylus pen which is operated by the test subject, but it is also possible for the contact part 80 to be anything that can draw a picture (such as a finger of the test subject), provided that it is possible to draw a trajectory by moving the contact part 80 in contact with the display surface of the TMT test image I.

The test data acquisition circuit 40 includes: i) a coordinate data acquisition circuit 42 that acquires coordinate data according to the position of the contact part 80 on the coordinate plane, based on the detection signal from the sensor 14 that detects the contact of the contact part 80 with the display surface of the TMT test image I; ii) a time data acquisition circuit 44 that uses a timer 16 to acquire the time data associated with the acquisition time of each coordinate data. Further, the data processing circuit 50 includes: i) an arithmetic circuit 52 that calculates a predetermined test value (for example, a test value related to the movement (or speed of movement) of the contact part) based on the coordinate data and the time data in the contact part 80; ii) an image generation circuit 54 that generates a characteristic image which, in association with the position of the transit point P, displays a time-dependent change of the test value calculated by the arithmetic circuit 52; iii) an image output circuit 58 that outputs a processed image including a characteristic image generated by the image generation circuit 54. Here, the characteristic image is a visual representation of the result of the TMT test performed by the test subject so that an evaluator can easily perform the evaluation, and an image that has displayed a time-dependent change of the test value in association with the position of transit point P.

Here, the sensor 14 may be any device having any detection principle as long as it can detect the contact of the contact part 80 with respect to the display surface of the TMT test image I. Further, although the sensor 14 is provided on the display 18 in this embodiment, it may also be provided on the contact part 80 side. Moreover, in the present embodiment, the sensor 14 can further detect the contact pressure of the contact part 80 with respect to the display surface of the TMT test image I.

Further, in the present embodiment, the image generation circuit 54 also includes an identification image generation circuit 56 that divides the coordinate plane into a plurality of regions determined based on the input signal from the mode selection menu 19, and generates characteristic images in a display form that can visually identify several sorts of data corresponding to respective regions. Further, the test data acquisition circuit 40 further includes a contact pressure data acquisition circuit 46 that acquires contact pressure data according to the position of the contact part 80 on the coordinate plane, in accordance with the detection signal from the sensor 14.

Further, the CPU 10 further includes: i) a transit detection circuit 32 that detects a transit through the transit point P based on the coordinates of the contact part 80 acquired by the coordinate data acquisition circuit 42 from the detection signal sent from the sensor 14; ii) a memory 20 including, for example, a RAM and/or a ROM that stores test data including coordinate data and time data acquired by the test data acquisition circuit 40 and processed images generated by the image generation circuit 54. The transit detection circuit 32 has a setting circuit 34 for variably setting a range for the coordinate region where it can be determined that the contact part 80 has passed through the transit point P.

Although the various circuits whose operations are controlled by the control circuit 30 are shown to be physically and individually provided in FIG. 1, it is also possible for a functional part (or a device) to be configured to integrate at least a part or all of these circuits (e.g., it is possible for all these circuits to be electronically included into one package). Namely, it is possible for these circuits to exist in any form, as long as the functionality of each of these circuits is ensured.

Figure 2:
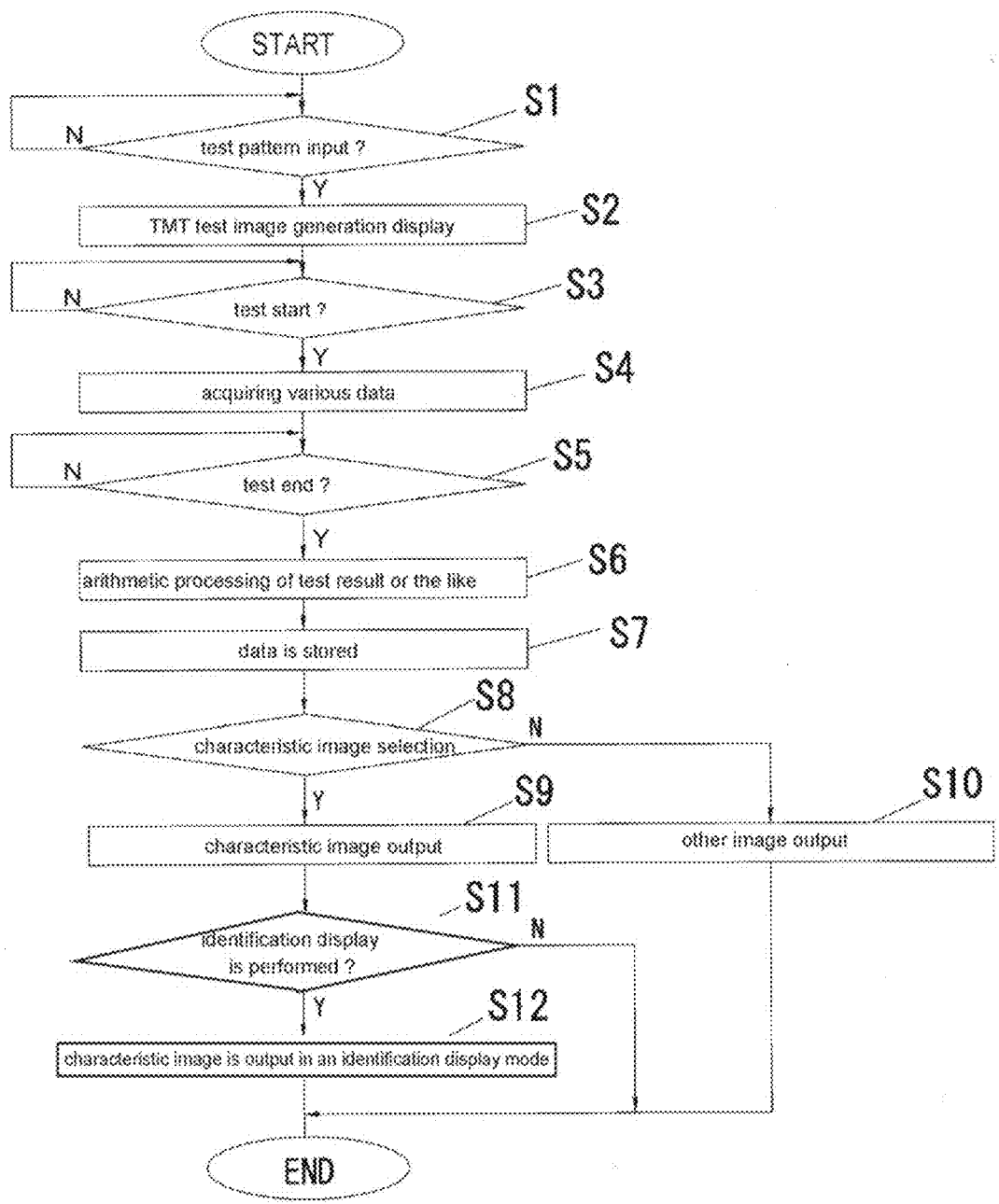
FIG. 2 is a flowchart schematically showing a flow of a process for performing a TMT test and displaying the test result using the TMT test result display system of FIG. 1.

Next, with reference to FIG. 2 (showing a flowchart) and FIGS. 3-23, description will be given to a process of performing the TMT test using the terminal 1 (TMT test result display system S) according to the present embodiment.

First, a system user (hereinafter, simply referred to as a user) who may be a test subject or an inspector such as a doctor, can perform a predetermined input on a display 18 of the terminal 1 which may be, for example, a touch panel, so that a mode selection menu 19 can be displayed on the display 18. For example, the mode selection menu 19 displays a user selection menu such as TMT-A test and TMT-B test. This display is performed by the display circuit 17 under the control of the control circuit 30, in accordance with the input signal from the display 18. Then, when the user selects a test mode of the TMT test through the mode selection menu 19 (step S1), the TMT test image I corresponding to the selection is displayed on the display 18. Specifically, for example, when the user selects TMT-A test on the mode selection menu 19, the test image generation circuit 25, in accordance with the input signal from the mode selection menu 19 (display 18), will electronically generate the TMT test image I for TMT-A test, which is formed by setting transit points at a plurality of positions on the coordinate plane. Then, the TMT test image I for TMT-A test is displayed as shown in FIG. 3(a) on the display 18, by using the display circuit 17 under the control of the control circuit 30. In particular, in the present embodiment, after the introduction screen of the TMT-A test shown on the upper side of FIG. 3(a) is displayed, the TMT test image I for the TMT-A test shown on the lower side of FIG. 3(a) is displayed (test image generation displaying step S2). At the time of execution of the test, the test subject moves the contact part 80 in contact with the display surface of the TMT test image I and connects them with lines in an order from 1 to 25, thereby measuring a time required for such completion (reaching 25) using a timer 16.

On the other hand, when the user selects TMT-B test on the mode selection menu 19, the test image generation circuit 25, in accordance with the input signal fed from the mode selection menu 19 (display 18), will electronically generate the TMT test image I for the TMT-B test, which is formed by setting transit points at a plurality of positions on the coordinate plane. Then, the TMT test image I for TMT-B test is displayed as shown in FIG. 3(*b*) on the display 18, by using the display circuit 17 under the control of the control circuit 30. Also in this case, after the introduction screen of the TMT-B test shown on the upper side of FIG. 3(*b*) is displayed, the TMT test image I for the TMT-B test shown on the lower side of FIG. 3(*b*) is displayed. As shown in the figure, the TMT test image I for the TMT-B test includes 13 numbers from 1 to 13 and 12 corresponding hiragana (a, i, u . . . sa, shi), and are randomly placed as transit points P based on a predetermined rule. When the test is executed, the test subject moves the contact part 80 in contact with the display surface of the TMT test image I, connects the numbers and the hiragana in an order using a line, thereby measuring a time required for such completion (reaching 13) using a timer 16.

Figure 4:
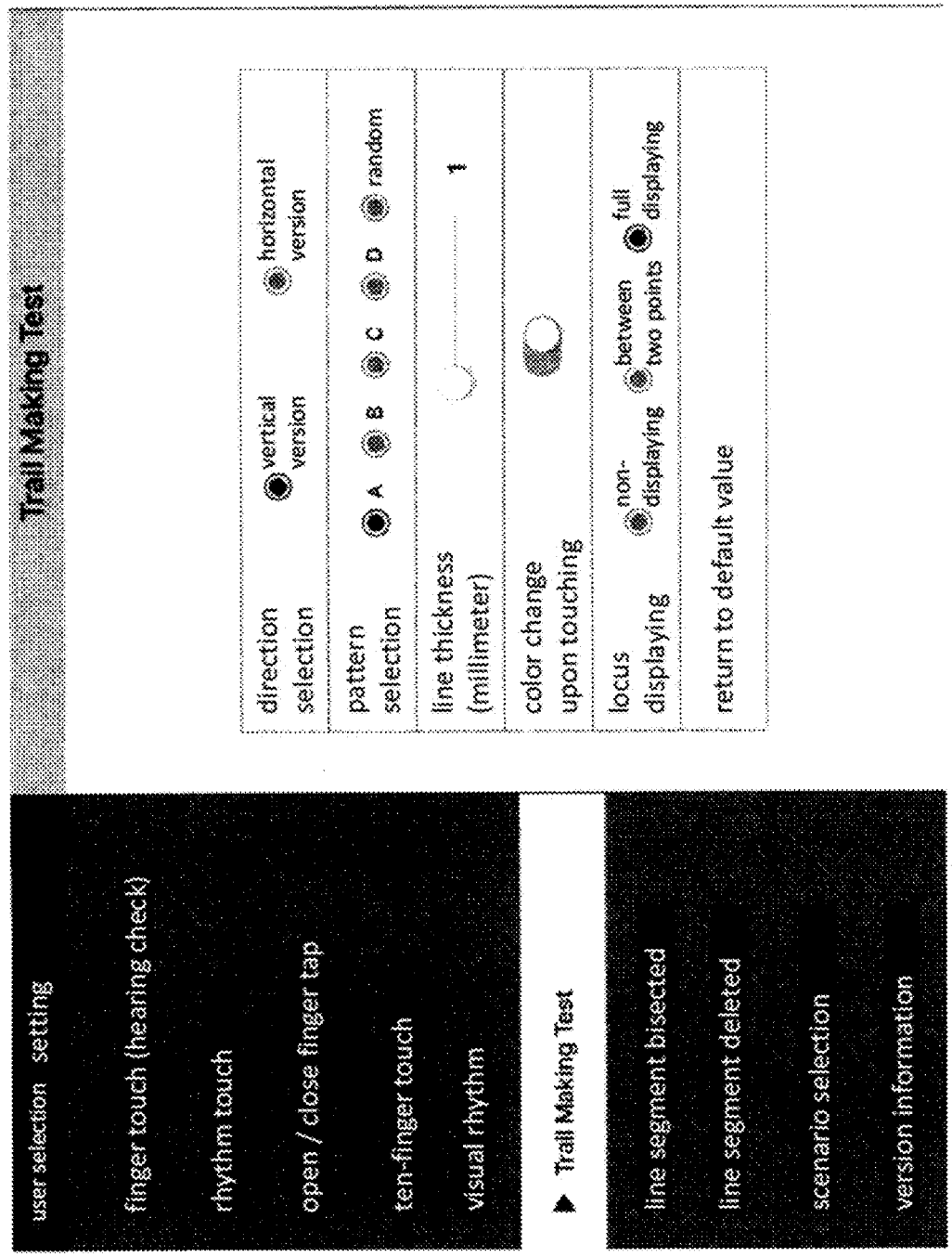
FIG. 4 shows an example of a display setting screen displayed on a display.
Figure 5B:
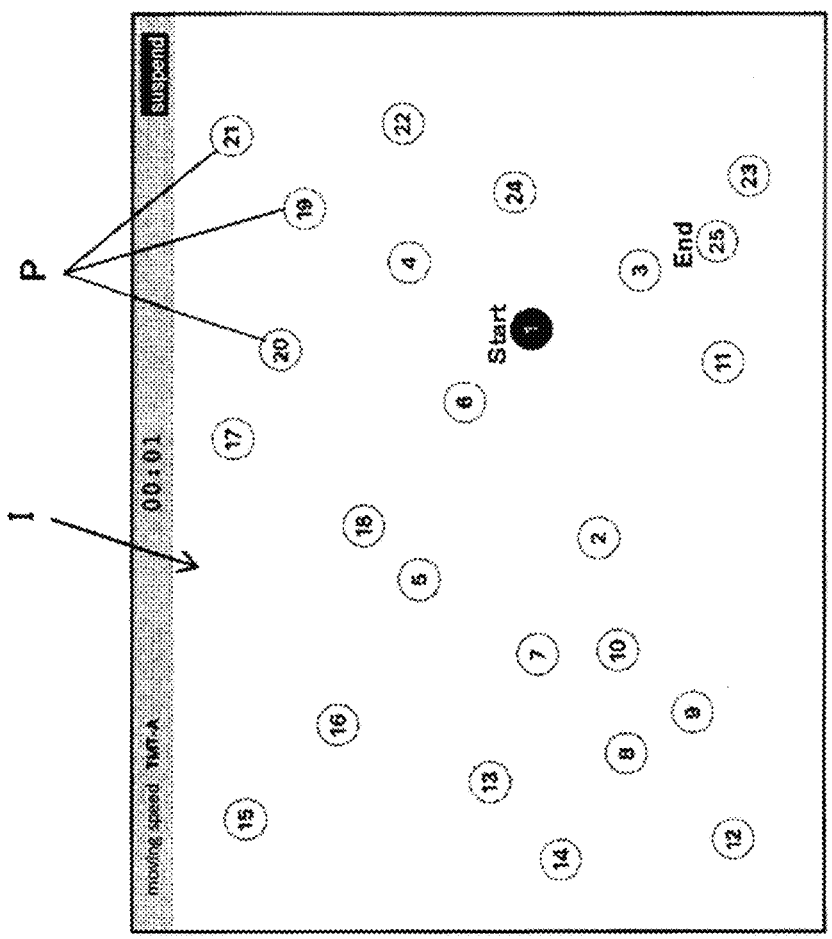
FIG. 5(b) shows an example of the TMT test image when the direction of horizontal version is selected on the display setting screen of FIG. 4.
Figure 5A:
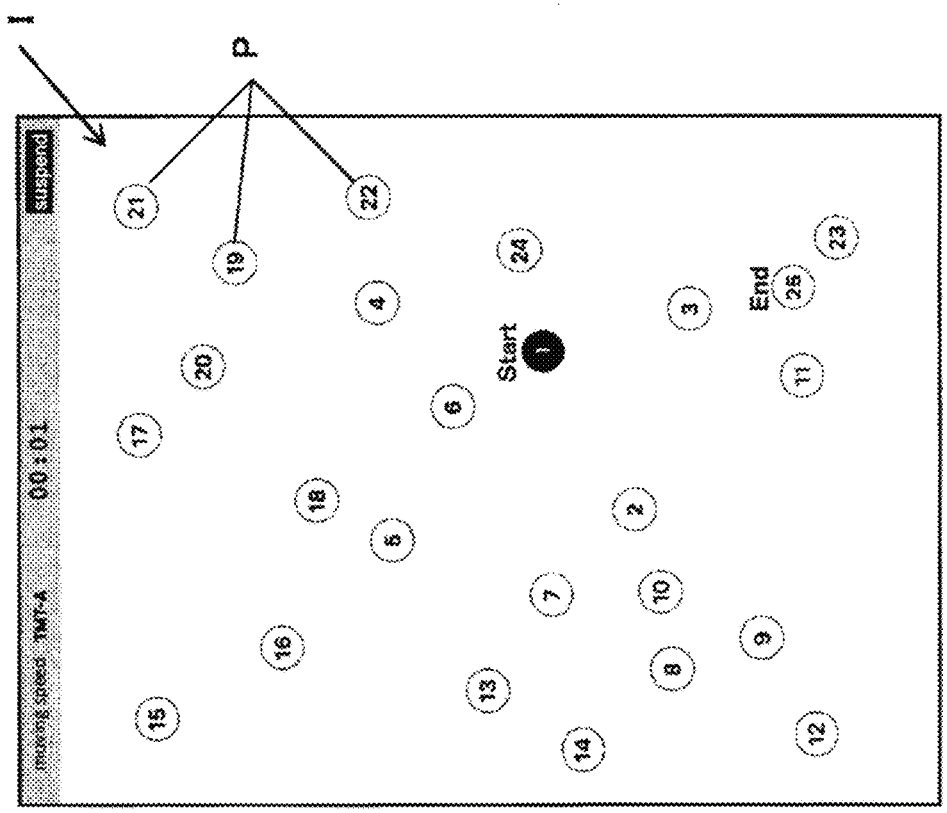
FIG. 5(a) shows an example of a TMT test image when the direction of vertical version is selected on the display setting screen of FIG. 4.

Further, at the start of such TMT test, the user performs a predetermined input on, for example, a touch panel of the display 18 of the terminal 1 to produce a TMT test display setting screen as shown in FIG. 4, thereby performing various settings in connection with display. Specifically, for example, when the direction of the vertical version is selected on the display setting screen of FIG. 4, the TMT test image I is displayed vertically on the display 18, by virtue of the display circuit 17 under the control of the control circuit 30 as shown in FIG. 5(*a*). On the other hand, when the horizontal version of direction is selected on the display setting screen of FIG. 4, the TMT test image I is displayed horizontally as shown in FIG. 5(*b*). Further, when the pattern A is selected on the display setting screen of FIG. 4, under the control of the control circuit 30, the test image generation circuit 25 and the display circuit 17 will operate to display the TMT test Image I on the display 18, as shown in FIG. 6(*a*). When the pattern B is selected on the display setting screen of FIG. 4, the TMT test image I inverted left and right with respect to the pattern A shown in FIG. 6(*b*) is displayed on the display 18. When the pattern C is selected on the display setting screen of FIG. 4, the TMT test image I inverted upside down with respect to the pattern A shown in FIG. 6(*c*) is displayed on the display 18. When the pattern D is selected on the display setting screen of FIG. 4, the TMT test image I whose top-bottom and left-right are inverted with respect to the pattern A shown in FIG. 6(*d*) is displayed on the display 18. When a random selection is performed on the display setting screen of FIG. 4, the TMT test image I of the pattern randomly determined by the control circuit 30 from the patterns A to D is displayed on the display 18.

Further, on the display setting screen of FIG. 4, it is possible to arbitrarily set a display form in which the display line of the drawing locus drawn by the test subject on the display surface of the TMT test image I is gradually thickened from, for example, stage 1 to stage 5 (for example, it is possible to set in millimeters). For example, when the thickness of the display line is set to the first stage on the display setting screen of FIG. 4, under the control of the control circuit 30, the display line of the drawing locus T shown in FIG. 7(*a*) is displayed on the TMT test image I by the display circuit 17. When the thickness of the display line is set to the second stage on the display setting screen of FIG. 4, the display line of the drawing locus T shown in FIG. 7(*b*) is displayed on the TMT test image I. When the thickness of the display line is set to the third stage on the display setting screen of FIG. 4, the display line of the drawing locus T shown in FIG. 7(*c*) is displayed on the TMT test image I. When the thickness of the display line is set to the fourth stage on the display setting screen of FIG. 4, the display line of the drawing locus T shown in FIG. 7(*d*) is displayed on the TMT test image I. When the thickness of the display line is set to the fifth stage on the display setting screen of FIG. 4, the display line of the drawing locus T shown in FIG. 7(*e*) is displayed on the TMT test image I.

Figure 8B:
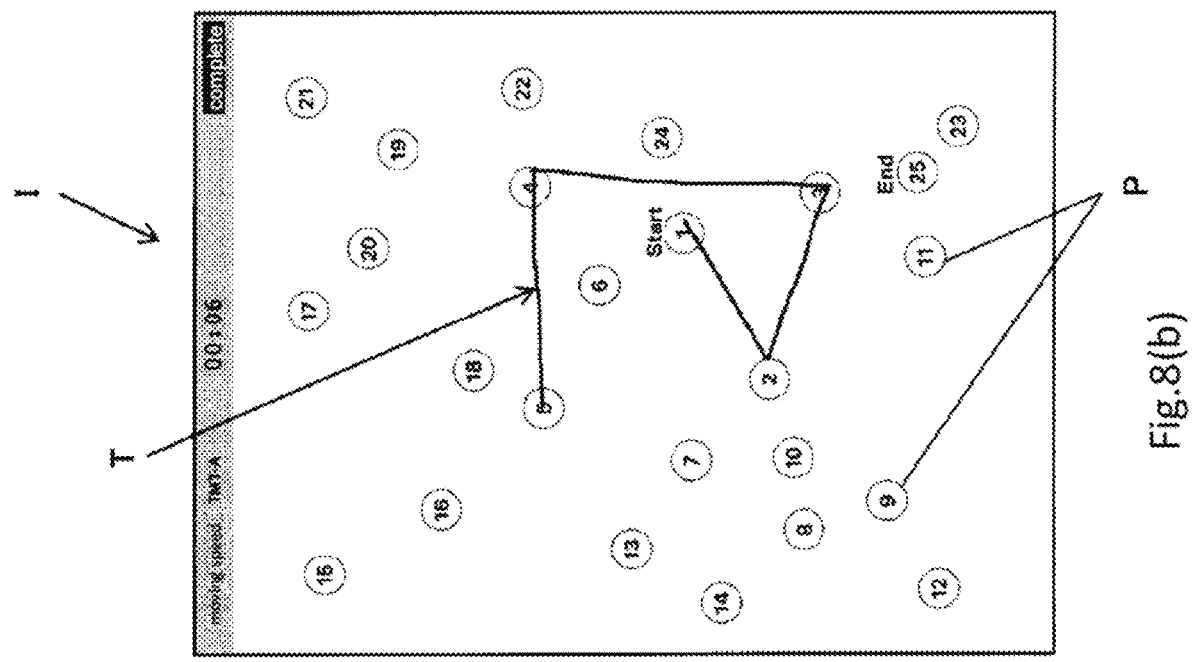
FIG. 8(b) shows a drawing trajectory on a TMT test image when a setting has been performed on the display setting screen of FIG. 4 which allows the color of the transit point to be not changed when the contact part has touched the transit point (has passed through the transit point).
Figure 8A:
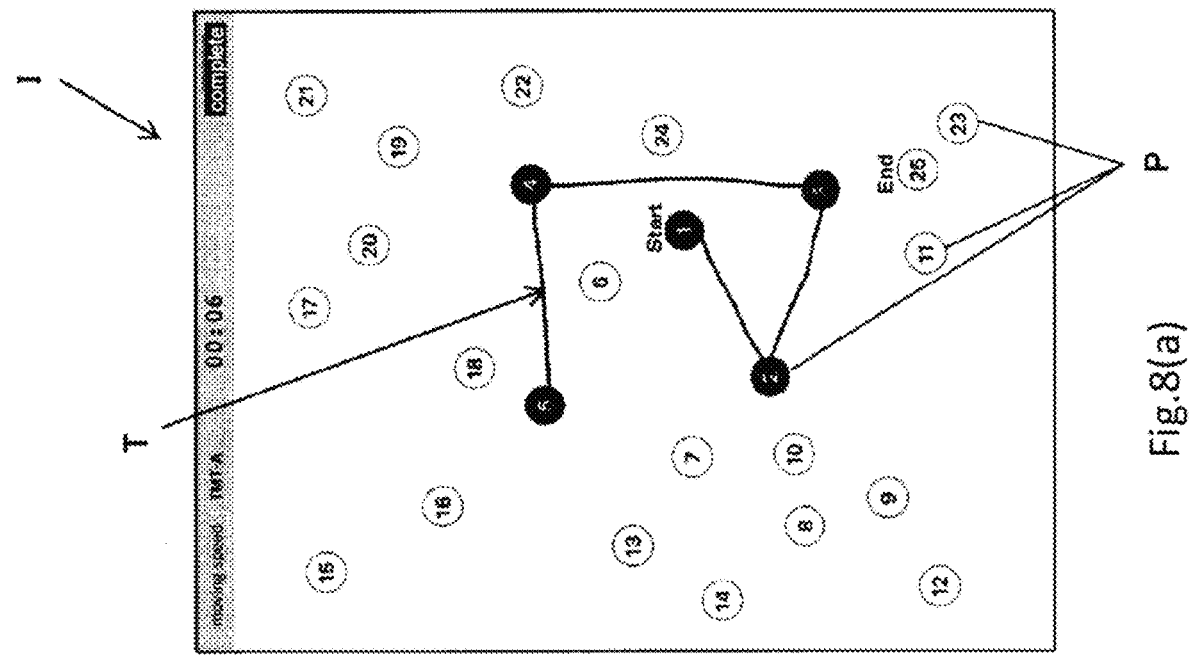
FIG. 8(a) shows a drawing trajectory on a TMT test image when a setting has been performed on the display setting screen of FIG. 4 which allows the color of the transit point to be changed when the contact part has touched the transit point (has passed through the transit point).

Further, on the display setting screen of FIG. 4, it is possible to set whether or not to change the color of the transit point P (to set a color change at the time of touch) when the contact part 80 comes into contact with the transit point P (passes through the transit point P). Specifically, when the color change of the transit point P is set when the contact part 80 passes (contacts) through the transit point P on the display setting screen of FIG. 4, under the control of the control circuit 30 and by virtue of the display circuit 17, the color of the transit point P passed by the contact part 80 that draws the drawing locus T on the TMT test image I is changed (as shown, the color is changed, and the circled numbers which are points P are painted black), as shown in FIG. 8(*a*). On the other hand, when a setting is performed on the display setting screen of FIG. 4, which does not change the color of the transit point P when the contact part 80 passes through (contacts) the transit point P, there will be no change in the color of the transit point P passed by the contact part 80 that draws the drawing locus T on the test image I, as shown in FIG. 8(*b*).

Figure 9A:
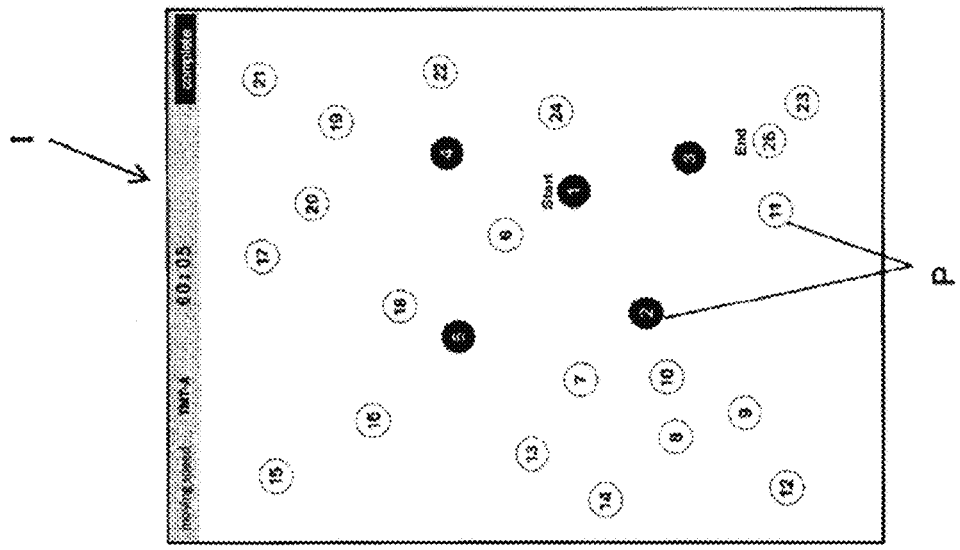
FIG. 9(a) shows a TMT test image when a setting for not visually displaying a drawing locus of a test subject is made on the display setting screen of FIG. 4.
Figure 9B:
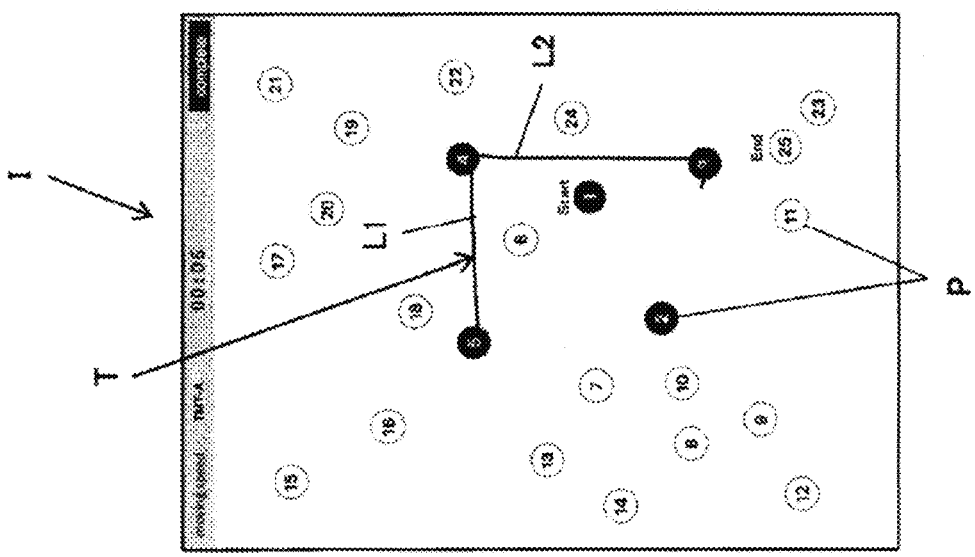
FIG. 9(b) shows the TMT test image when a setting is performed on the display setting screen of FIG. 4 which visually displays the drawing trajectory of the test subject only between the latest two transit points (between the last transit point at the present time during drawing and a transit point immediately before it).
Figure 9C:
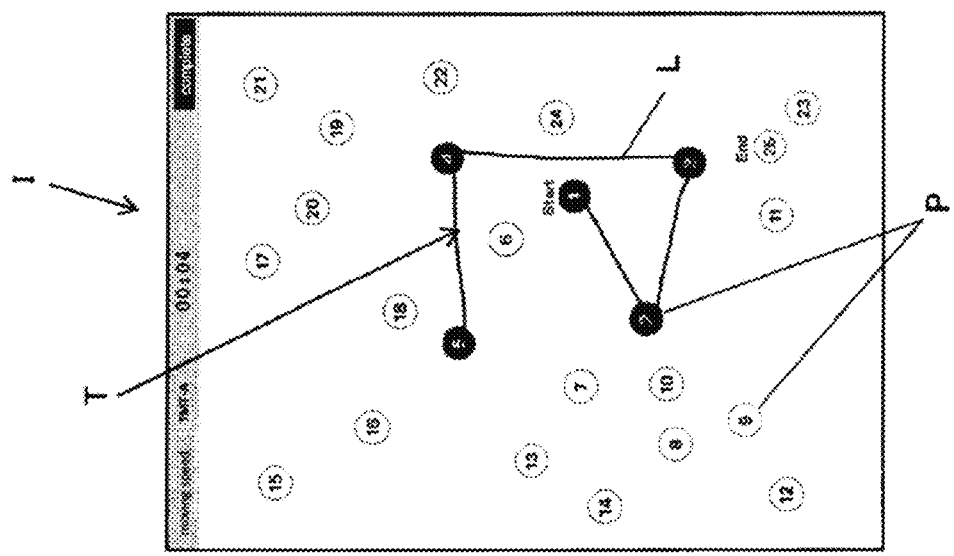
FIG. 9(c) shows a TMT test image when a setting for visually displaying the drawing locus of a test subject among all the transit points is performed on the display setting screen of FIG. 4.

Further, on the display setting screen of FIG. 4, it is also possible to set a display mode of drawing locus (which is drawn by the test subject). Specifically, when the display mode of the drawing locus is set at "non-display" (the drawing locus of the test subject is not visually displayed), under the control of the control circuit 30 and by virtue of the display circuit 17, even if the test subject moves the contact part 80 to draw a drawing locus, it is not displayed as a display line (however, as shown in the figure, the communication point P that the contact part 80 has already passed through may change its color), as shown in FIG. 9(*a*). Moreover, when the display mode of the drawing locus is set at "between two points", as shown in FIG. 9(*b*), the drawing locus T of the test subject is visually displayed as a display line only between the latest two transit points P (a transit point P that was last passed through and a transit point P that was passed through immediately before the last). For example, in this figure, when the contact part 80 reaches the transit point P of the number 5, the display line L2 connecting the transit point P of the number 3 and the transit pattern P of the number 4 will disappear. At this time, only the display line L1 connecting the transit point P of the number 3 and the transit pattern P of the number 4 will remain (however, as shown in the figure, the communication point P already passed through by the contact part 80 may change its color). Moreover, when the display mode of the drawing locus is set at "all display" (all of the drawing locus of the test subject are visually displayed), the test subject can move the contact part as shown in FIG. 9(*c*), and the entire drawing locus drawn over time is displayed as the display line L (for example, as shown in the figure, the communication point P that has already been passed through by the contact part 80 will change its color). In addition, on the display setting screen of FIG. 4, it is also possible to return to the initial setting (default). Further, the test subject may be able to practice the TMT test by an exercise screen prepared in advance prior to the start of the TMT test.

When the TMT test described above is started by the test subject (step 3), the test data acquisition circuit 40 moves the contact part 80 in contact with the display surface of the TMT test image I, and traces the transit points P in a predetermined order, thereby obtaining data of the locus drawn over time (test data acquisition step S4). Specifically, in this test data acquisition step, the coordinate data acquisition circuit 42, in accordance with the detection signal from the sensor 14 that detects the contact of the contact part 80 with the display surface of the TMT test image I, acquires the coordinate data according to the position of the contact part 80 on the coordinate plane (coordinate data acquisition step), while the time data acquisition circuit 44 acquires the time data associated with the acquisition time of each coordinate data by using the timer 16 (time data acquisition step).

Figure 15:
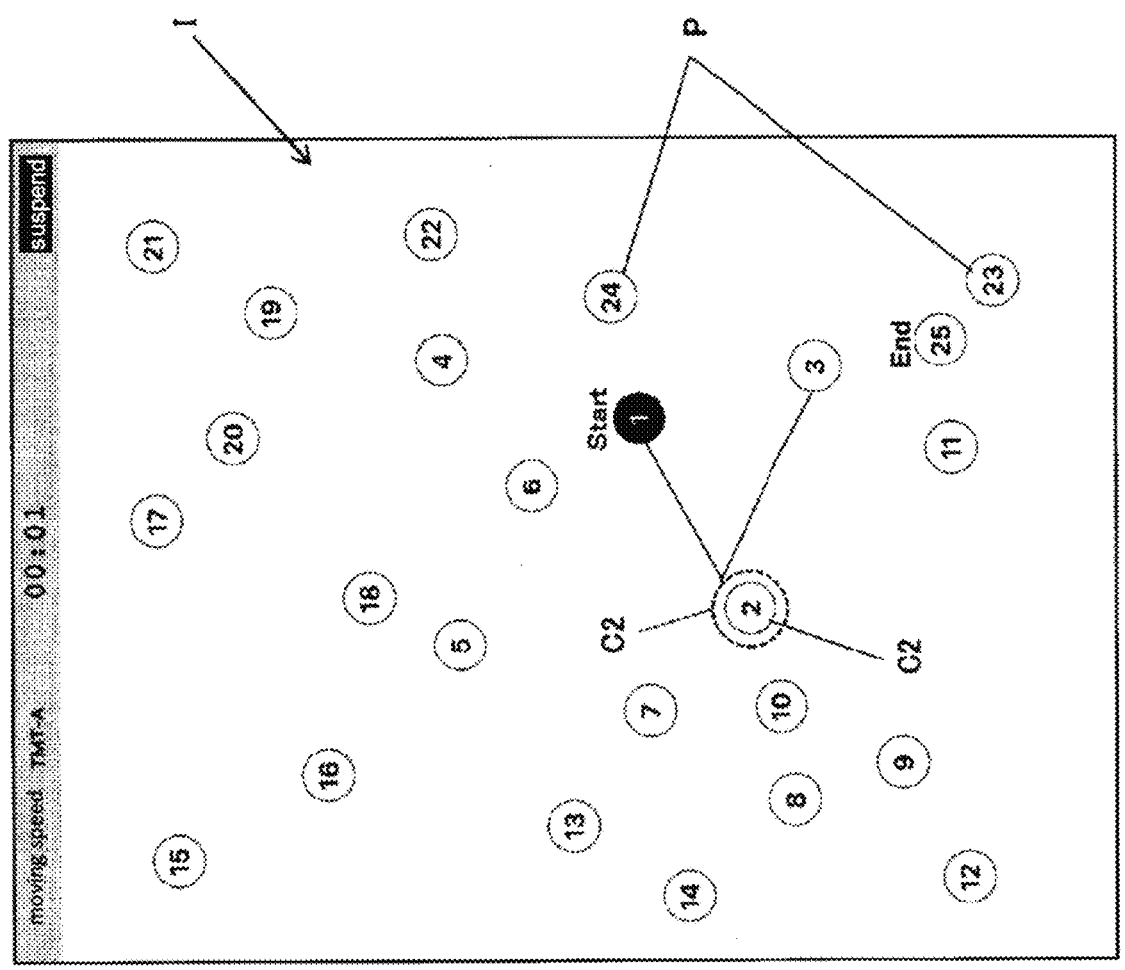
FIG. 15 is an explanatory diagram for explaining on the TMT test image that it is possible to variably set a range for the coordinate region where it can be determined that the contact part has passed through transit point.

Here, in view of the passing through the transit point P by the contact part 80 during the TMT test, as described above, the transit detection circuit 32, in accordance with the coordinates of the contact part 80 acquired by the coordinate data acquisition circuit 42 from the detection signal fed from the sensor 14, detects the passing through the transit point P by the contact part 80 (transit detection step). At this time, the transit detection circuit 32 detects the passing in accordance with the value set by the setting circuit 34 (namely, the setting range of the coordinate region where it can be determined that the contact part 80 has passed through the transit point P). Specifically, for example, as shown in FIG. 15, the transit points (numbers 1 to 25) P are displayed as a circular region in the TMT test image I. Apparently in the image, the range of the coordinate region where it can be determined that the contact part 80 has passed through the transit point P is defined as the coordinate region inside the reference circle C11 (solid circle in the figure) which is a circular region). Even under such a condition, if, for example, a virtual circle C2 (in the figure, a circle indicated by a broken line surrounding the solid reference circle C1 from the outside) having a radius X % larger than the radius of the reference circle is set in the setting circuit 34, the transit detection circuit 32 can judge that the contact part 80 has passed through the transit point P even if the contact part 80 has not passed through the inside of the reference circle C1 (as long as it passes through the region inside the virtual circle C2). In this case, the value set in the setting circuit 34 can be changed by the user selecting, for example, the value of X in the range of 0 to the predetermined value on the predetermined setting screen displayed on the display 18.

According to such a configuration, it is possible not only to detect a passing through the transit point P using the contact part 80 (by virtue of the cooperation between the sensor 14 and the transit detection circuit 32), but also to set an allowable range for determining whether or not the contact part 80 has passed through the transit point P by using the setting circuit 34. In this case, while it is possible to give a discretion to the transit judgment, it is also possible to impose a certain restriction on the discretion by defining a variable setting range for coordinates. Further, it is possible to carryout a test with a degree of freedom according to an actual situation, while at the same time minimizing a fluctuation in the test result which is caused due to the discretion.

Then, when the TMT test by the test subject is completed (step S5) (or in parallel with the TMT test), the data processing circuit 50 processes the data acquired by the test data acquisition circuit 40 and allows the processing result to be displayed as a test result on the display 18 (data processing display step). Specifically, the arithmetic circuit 52 of the data processing circuit 50 calculates test values related to the movement of the contact part 80 in accordance with the coordinate data and the time data (calculation step S6), and these test values are stored in the memory 20 (storing step S7). Meanwhile, based on the output image selection by the user (selection of whether to output a characteristic image or a selection of whether to output another processed image; step S8), the image generation circuit 54 generates a characteristic image (image generation step) which displays a time-dependent change of the test value calculated by the arithmetic circuit 52 (in association with the position of transit point P), or generates another processed image, while the image output circuit 58 outputs a processed image including the characteristic image generated by the image generation circuit 54, thereby displaying the image on the display 18 (image output display steps S9 to S12)

Figure 14:
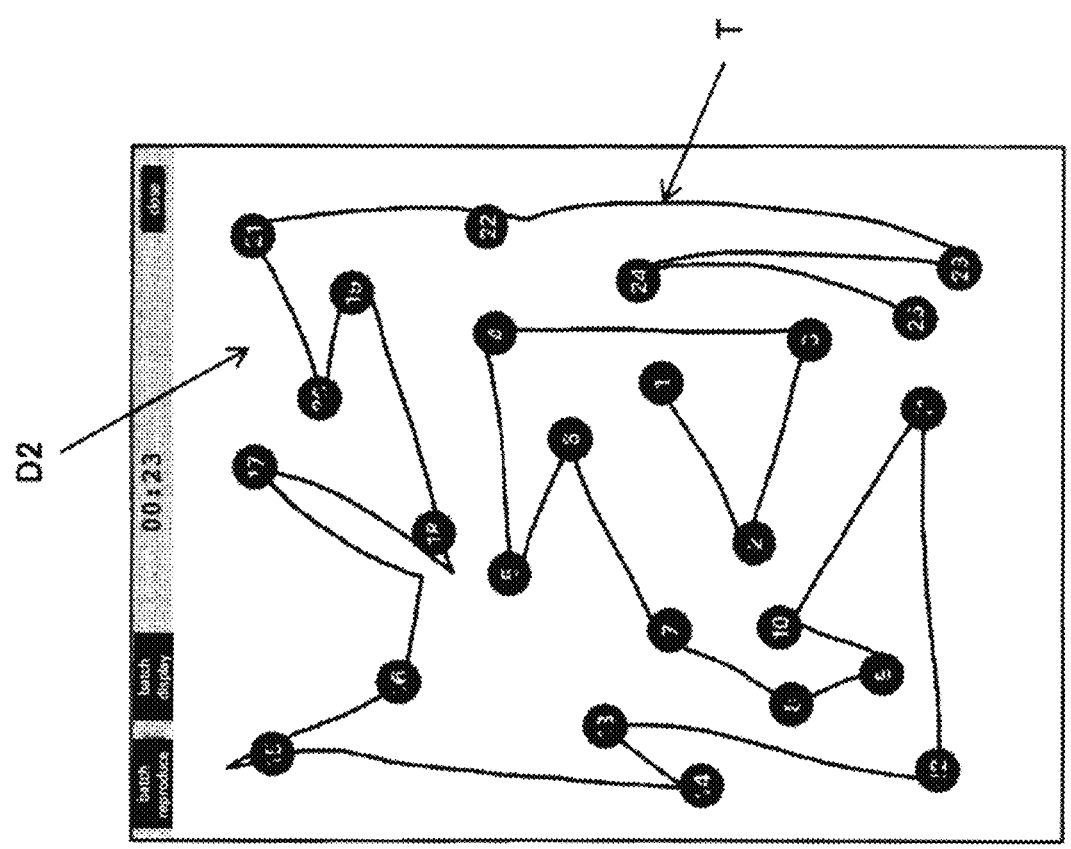
FIG. 14 shows an example of a drawing locus reproduction image (moving image) that dynamically displays the entire path of a drawing locus drawn by a test subject.

Here, the test values (calculated by the arithmetic circuit 52) related to the movement of the contact part 80 may be, for example, a speed, an acceleration, a jerk degree of the contact part 80, and a time for passing through the transit point P by the contact part 80, as well as a required time between the transit points P. Therefore, in the terminal 1 (TMT test result display system S) according to the present embodiment, a processed image shown in FIG. 10(*a*) is displayed as a test result on the display 18, in accordance with the processing performed by the data processing circuit 50. The processed image shown in FIG. 10(*a*) is displayed on the display 18 by, for example, performing a predetermined input on the touch panel of the display 18 and selecting a display form of the test result from the mode selection menu 19. In this processed image, it is possible to display a time for passing through each transit point P by the contact part 80 and some time differences between these passing times (a time required for contact part 80 to move between the transit points P) as numerical data D1, in association with the transit points P (numbers 1 to 25). Meanwhile, the test subject moves the contact part 80 so that the entire drawing locus T drawn over time is displayed as still image data D2 (which may be a reproduced moving image), or may be displayed individually as shown in FIG. 14. On the other hand, in the terminal 1 of the present embodiment, it is possible to freely move from this test result screen to a user setting screen such as the mode selection menu 19, and it is also possible to detect an error in the test progress by the test subject and display the error (as a test result after test) on the display 18. Alternatively, during test it is possible to display in real time an error as part of TMT test image on the display 18.

Figure 17:
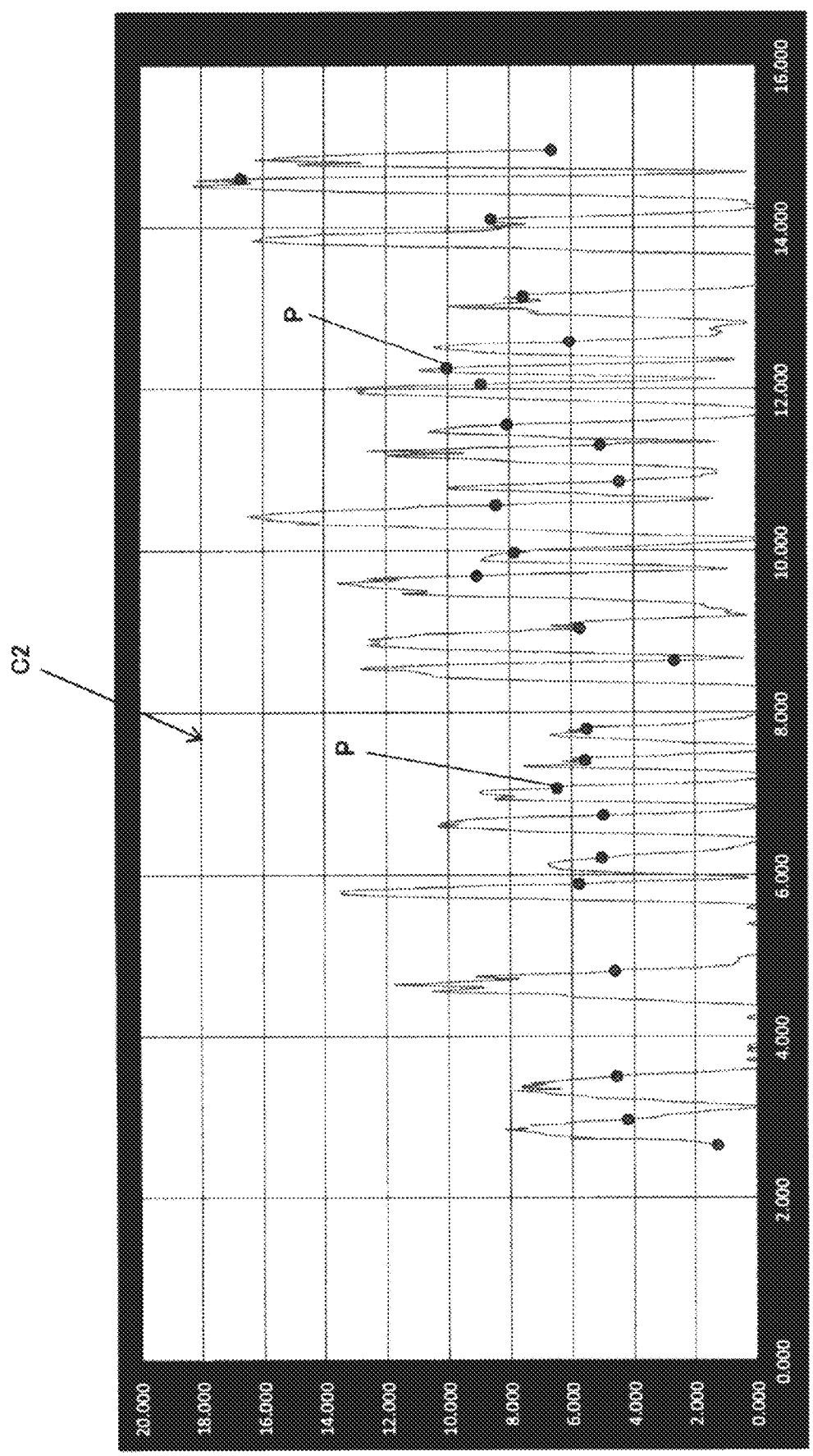
FIG. 17 is an example of a characteristic image displayed as a test result on a display (a characteristic image in which a time-dependent change in the speed of movement of a contact part during drawing by a subject is displayed in association with the position of a transit point).
Figure 20:
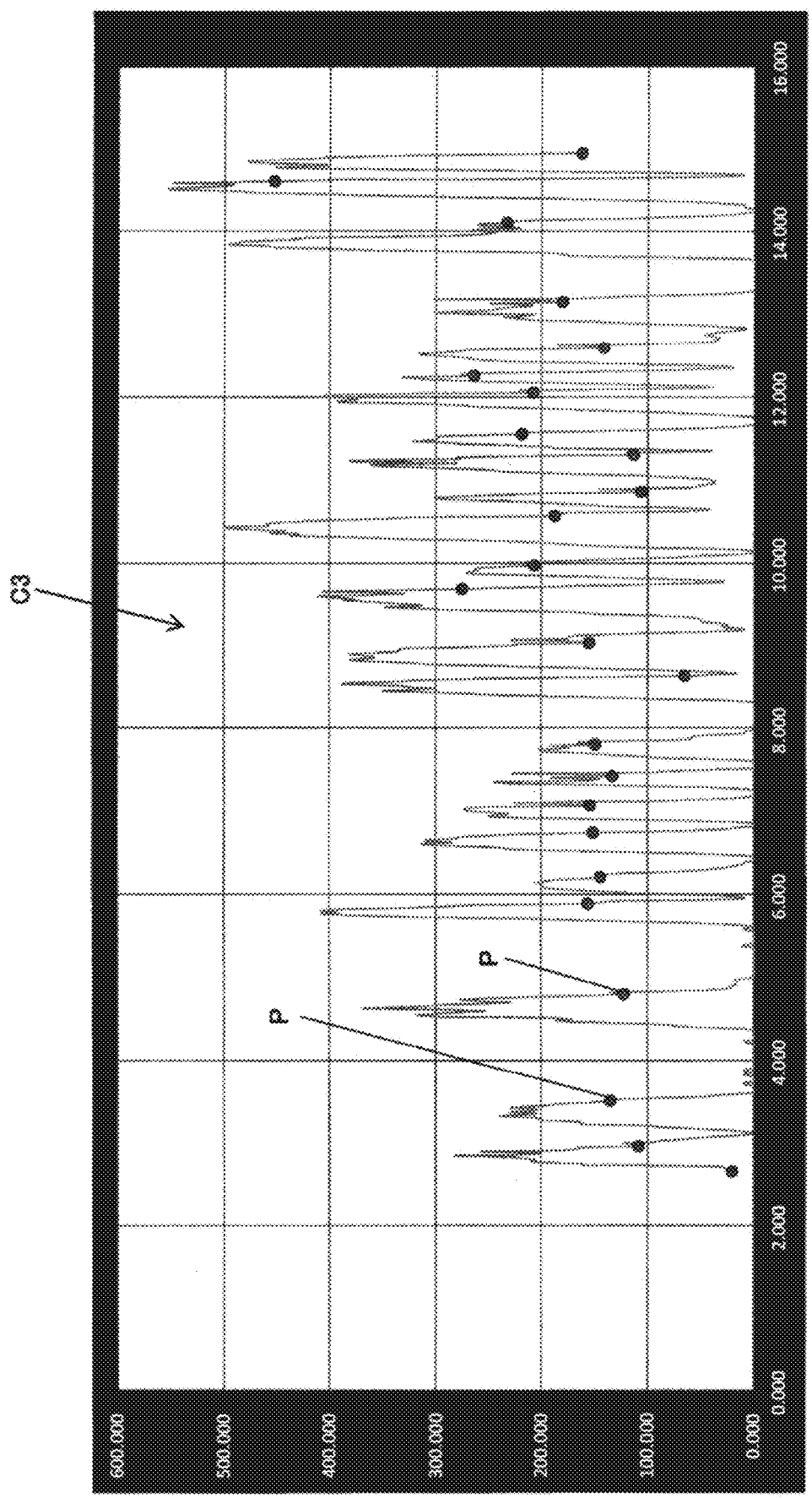
FIG. 20 is an example of a characteristic image displayed as a test result on a display (a characteristic image in which a time-dependent change in acceleration of movement of a contact part during drawing by a subject is displayed in association with a position of a transit point).
Figure 21:
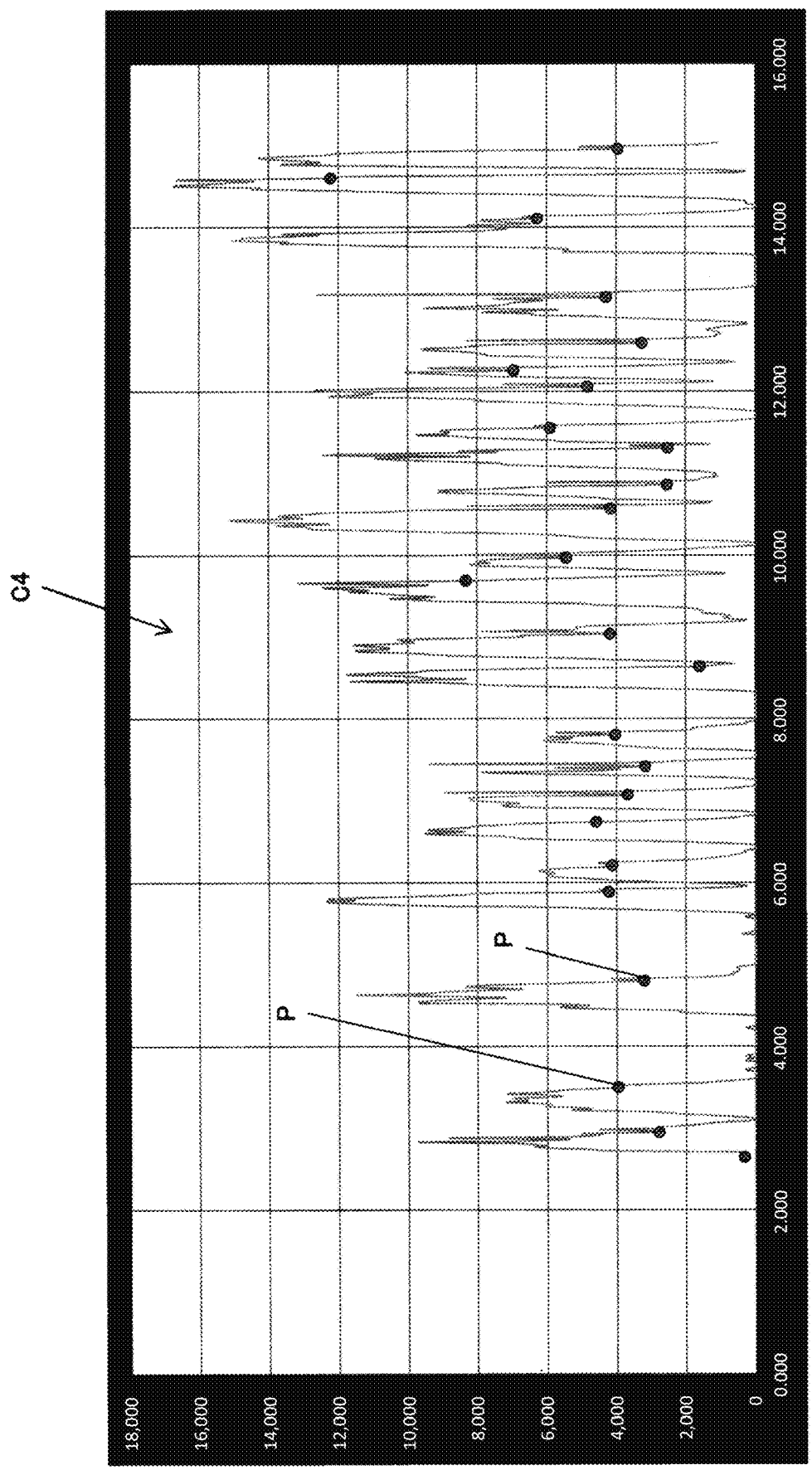
FIG. 21 is an example of a characteristic image displayed as a test result on a display (a characteristic image in which a time-dependent change in the jerk degree in the movement of a contact part during drawing by a test subject is displayed in association with the position of a transit point).
Figure 22:
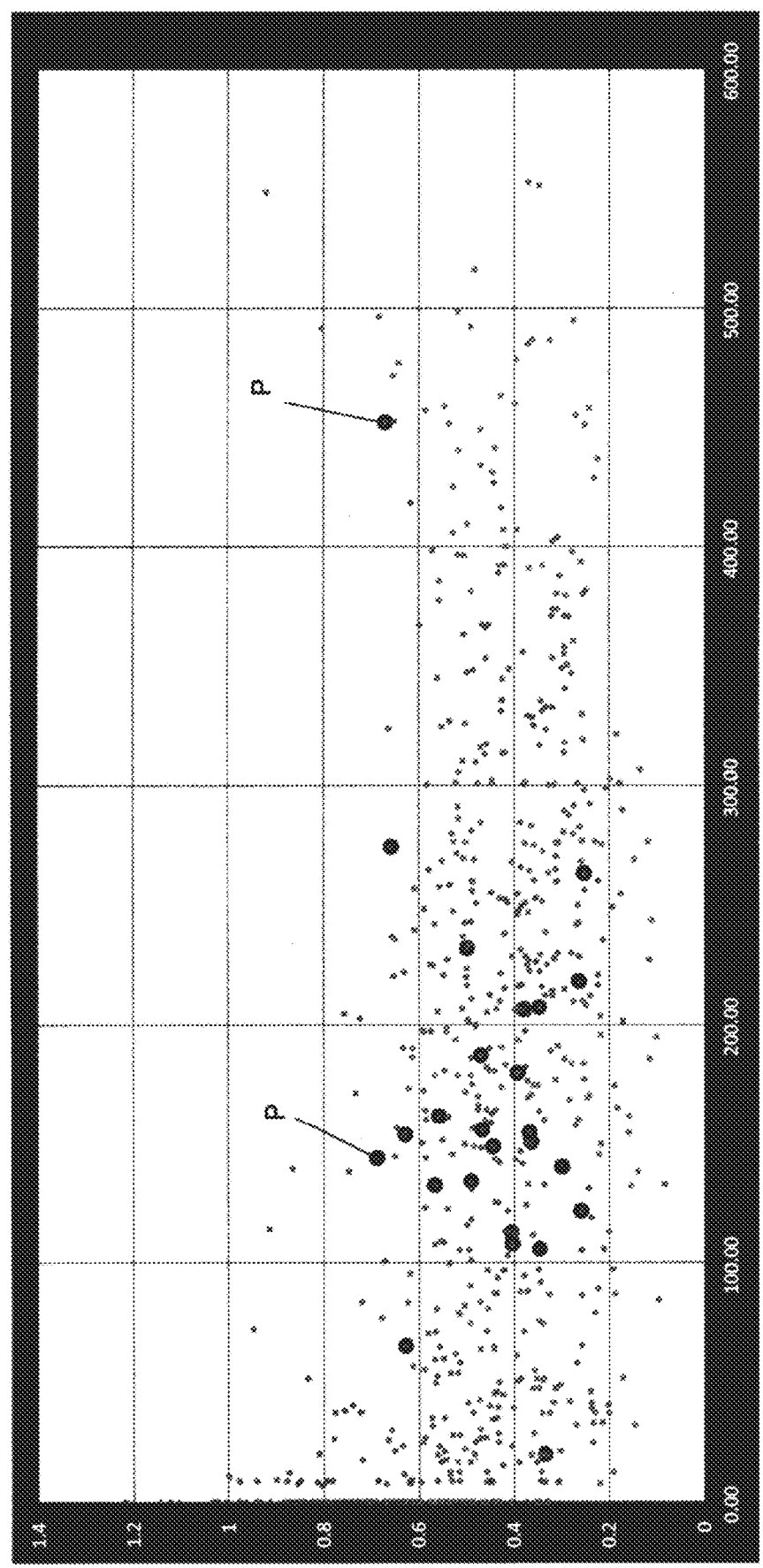
FIG. 22 is an example of a processed image displayed as a test result on a display (an image displaying a relationship between the contact pressure and acceleration of a contact part with respect to the display surface of the TMT test image is displayed in association with the position of a transit point).

FIG. 10(*b*) shows an example of a characteristic image that displays a time-dependent change for a test value calculated by the arithmetic circuit 52 in association with the positions of the transit points P. Also, this characteristic image 01 displays a time-dependent change of a time for passing through the transit point P by the contact part 80 (in association with the position of transit point P). In the characteristic image 01, the horizontal axis shows the transit points (numbers 1 to 25), and the vertical axis shows a passing time. Further, FIG. 17 shows another example of characteristic image. This characteristic image C2 displays a time-dependent change in the speed of movement of the contact part during picture drawing by the test subject (in association with the position of transit point P). In the characteristic image C2, the horizontal axis shows time and the vertical axis shows speed. Further, in the characteristic image C2, each transit point (numbers 1 to 25) P is displayed here as a dot having a predetermined size on the velocity-time diagram. In addition, FIG. 20 shows yet another example of the characteristic image. This characteristic image C3 displays a time-dependent change in the acceleration of the movement of the contact part 80 during picture drawing by the test subject (in association with the position of transit point P). In the characteristic image C3, the horizontal axis represents time and the vertical axis represents an acceleration. Further, also in this characteristic image C3, each transit point (numbers 1 to 25) P is displayed as a dot having a predetermined size on the acceleration-time diagram. Moreover, FIG. 21 shows another example of the characteristic image. This characteristic image C4 displays a time-dependent change in the jerk degree of the movement of the contact part 80 during picture drawing by the test subject (in association with the position of transit point P). In the characteristic image C4, the horizontal axis shows time and the vertical axis shows jerk. Further, also in this characteristic image C4, each transit point (numbers 1 to 25) P is displayed as a dot of a predetermined size on the jerk-time diagram.

Further, in the terminal 1 of the present embodiment, the identification image generation circuit 56 of the image generation circuit 54 divides the coordinate plane into a plurality of regions determined in accordance with the input signal fed from the mode selection menu 19, and it is possible to generate a characteristic image in a display form in which the data corresponding to the above each region thereof can be visually distinguished from each other (identification display step in the image generation step). Here, the "visually identifiable display form" is a display form that enables the data corresponding to each area to be visually distinguished from each other by making use of the differences in color, line type, pattern, and the like. Further, regarding the area dividing, it is possible for a user to perform a selection from the mode selection menu 19. Moreover, the control circuit 30, in accordance with the input signal fed from the mode selection menu 19 accompanying the selection, controls the identification image generation circuit 56 of the image generation circuit 54, thereby generating an identification display image. Specifically, when the user performs a predetermined input on the touch panel of the display 18, selects a display form of the test result from the mode selection menu 19, and further selects an identification display (step S11), the image generation circuit 54 will generate an identification display image (a processed image including a characteristic image forming the identification display form), by virtue of the identification image generation circuit 56 (subsequently, the identification display image is outputted according to step S12). On the other hand, if the identification display is not selected when selecting a display form of test result, the image generation circuit 54 will generate a processed image including a characteristic image without the identification display.

An example of the identification display image is shown in FIG. 13. Here, the identification display image F1 shown in FIG. 13(a) is a characteristic image in which a time required between the transit points P by the contact part 80 is displayed as a bar graph for each transit point P in the identification display form, while the coordinate plane of the TMT test image I is divided into two areas on the left and right. Namely, the coordinate plane is divided into a right side region consisting of the first and fourth quadrants and a left side region consisting of the second and third quadrants, and the data corresponding to the right side region and the left side region are color-coded in two colors (In the figure, the right area is shown in black and the left area is shown in white, but any color coding is acceptable). Further, the identification display image F2 shown in FIG. 13(b) also represents (in the identification display form) a characteristic image formed by displaying (in a bar graph) the time required between the transit points P by the contact part 80 for each transit point P. In this identification display image F2, as drawn in the lower left portion of FIG. 19, eight boundary straight lines are set, which extend radially from the coordinate origin of the TMT test image I and are separated from each other by equal angular intervals around the coordinate origin. Eight regions defined by these boundary lines are defined in the coordinate plane, and the data corresponding to each of these regions are color-coded by the number of colors corresponding to the number of regions (here, eight colors) (In the figure, for convenience, they are distinguished by eight different patterns).

Figure 18:
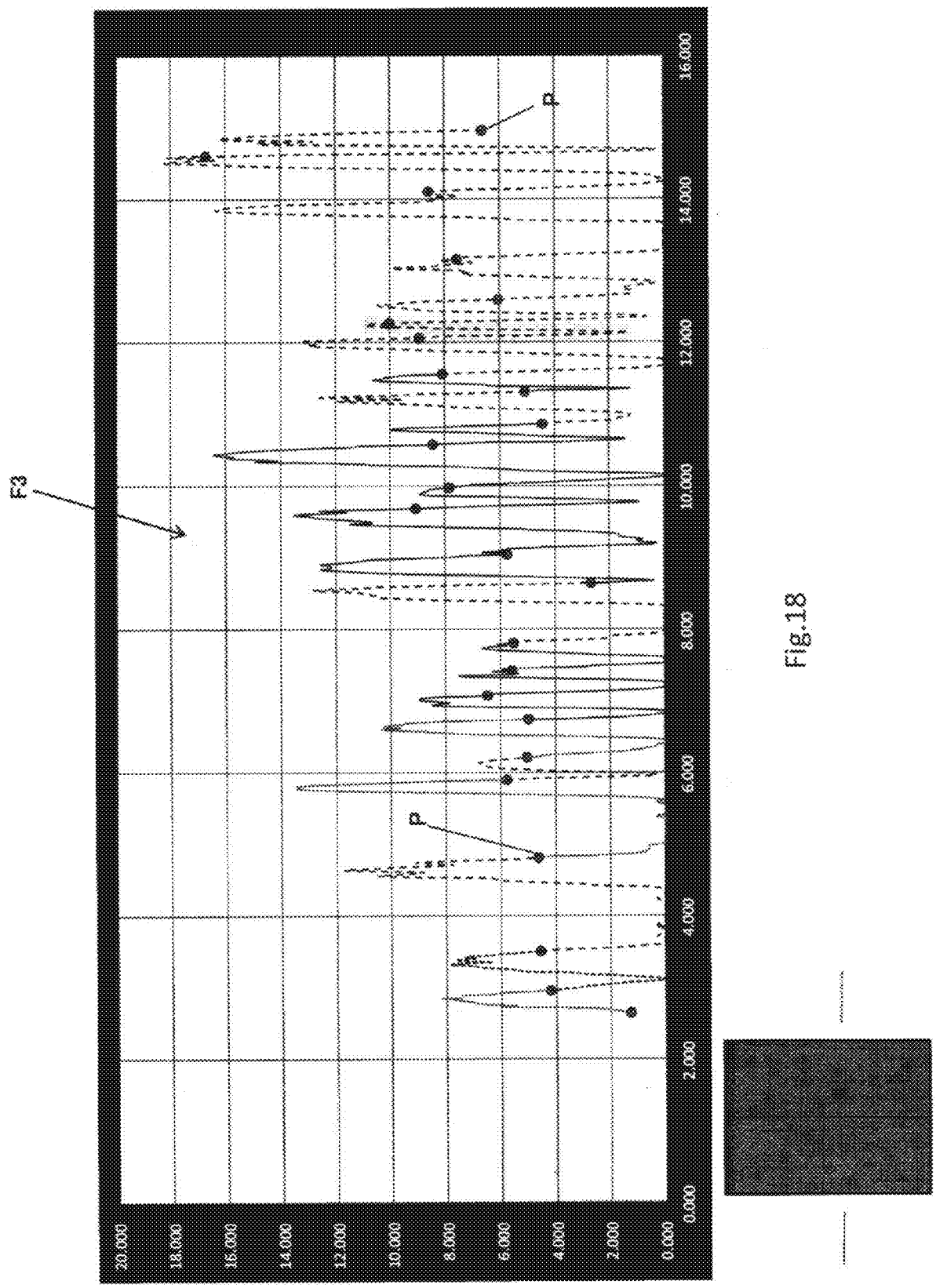
FIG. 18 shows an example of a display form of the characteristic image of FIG. 17, in which the coordinate plane of the TMT test image is divided into two left and right regions, and the data corresponding to each of the regions are visually distinguished from each other.
Figure 19:
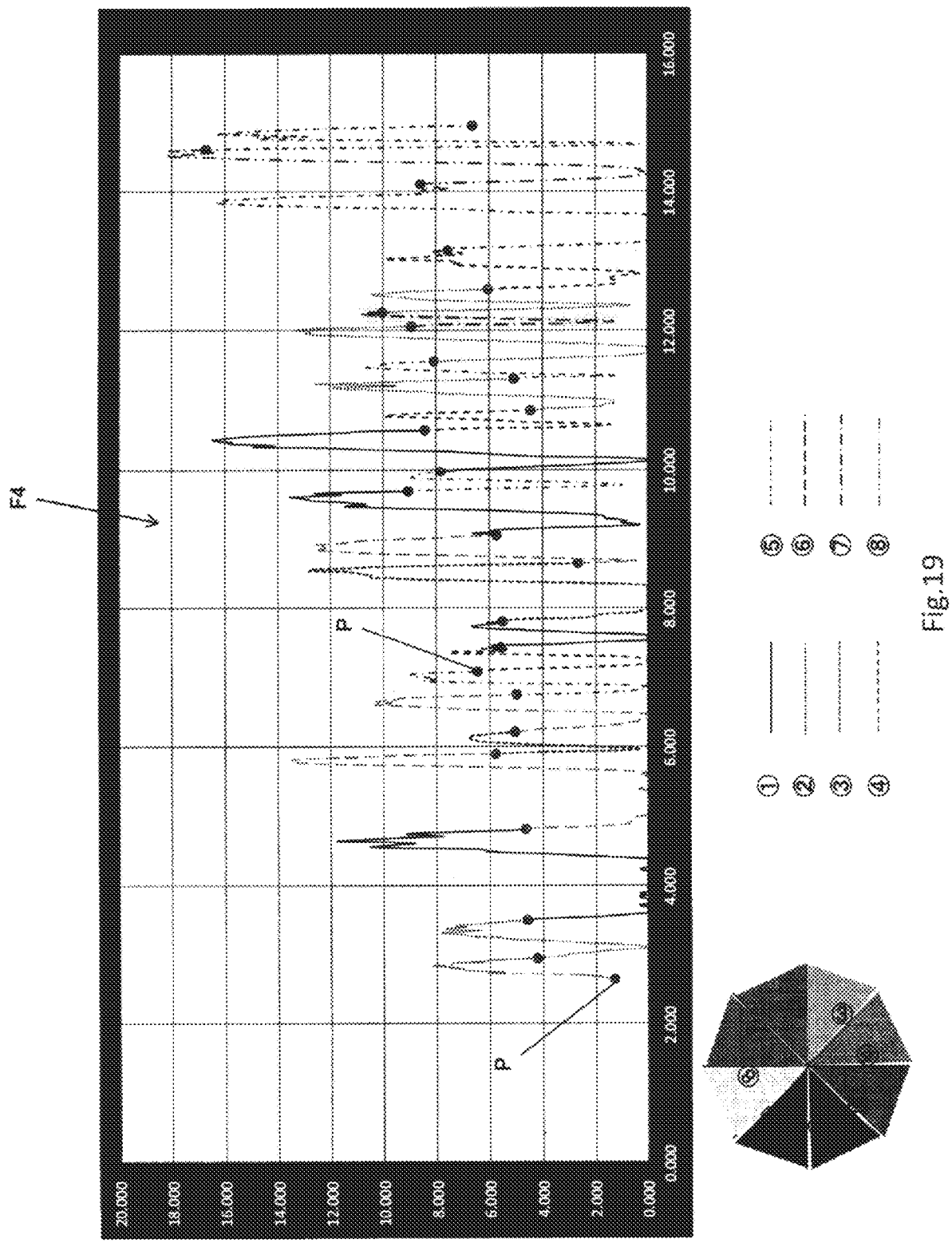
FIG. 19 is an example of a display form of the characteristic image of FIG. 17, in which the coordinate plane of the TMT test image is divided into eight regions in eight directions, and the data corresponding to each of these regions are displayed so as to be visually distinguishable from each other.

Other examples of the identification display image are shown in FIG. 18 and FIG. 19. The identification display image F3 shown in FIG. 18 divides the coordinate plane into two left and right regions, as in the case shown in FIG. 13(a), and is formed by color-coding the corresponding data into two colors (in the figure, for convenience, they are distinguished by a solid line (left side area) and a dotted line (right side area)). The corresponding data are corresponding to the right region and the left region respectively in the characteristic image C2 shown in FIG. 17. On the other hand, in the identification display image F4 shown in FIG. 19, the coordinate plane is divided into eight regions in eight directions as in the case of FIG. 13(b), and in the characteristic image C2 shown in FIG. 17 described above, data corresponding to each of the eight regions are color-coded by eight colors (in the figure, for convenience, they are distinguished by eight different types of line).

By identifying and displaying the characteristic image in this way, it is possible to grasp at a glance the tendency peculiar to the position and direction in the coordinate plane. For example, it is possible to visually clearly grasp at a glance the tendency of the test result depending on whether the subject's dominant hand is the left hand or the right hand, or the tendency of the test result due to the damaged part of the brain. Also, for example, it is possible to clearly visually grasp at a glance the tendency of test results due to the deterioration of visual acuity of one eye or due to the deterioration of local or overall physical function, thereby making it possible to easily evaluate the cognitive function of the test subject. In the present embodiment, it is also possible to perform a change-over on the on/off of the identification display (whether or not the identification display is to be performed) at all times.

Figure 23B:
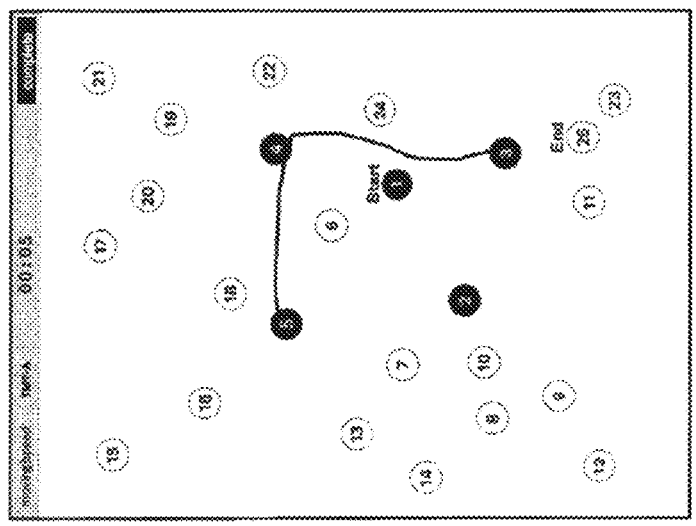
FIG. 23(b) shows an example of a drawing trajectory reproduction image (moving image) that dynamically displays the drawing trajectory drawn by the test subject in the transit point zone
Figure 23A:
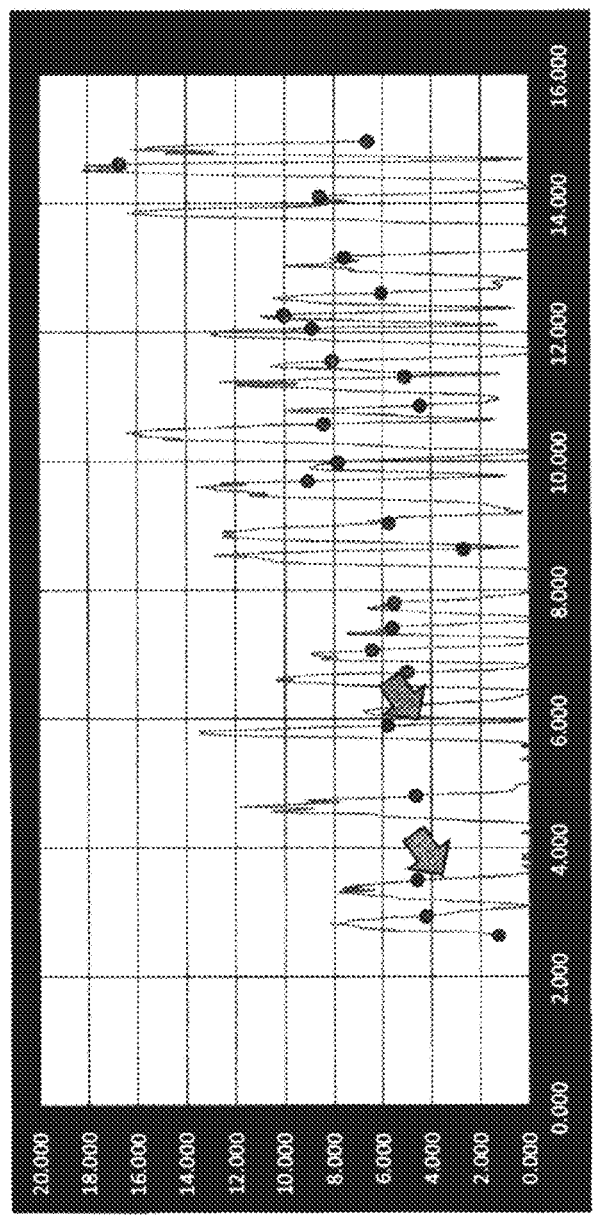
FIG. 23(a) shows an example of a display form in which an arrow is attached on the characteristic image shown in FIG. 17, showing a designated zone of a transit point.

Further, in the terminal 1 of the present embodiment, the image generation circuit 54 (image generation step) can generate a drawing locus reproduction image as a processed image. The drawing locus reproduction image can display dynamically and/or statically the drawing locus drawn by the contact part 80, in a predetermined zone which is determined in accordance with an input signal from the mode selection menu 19. In this case, the user can select the transit point zone to be reproduced, as the display form of the test result, from the mode selection menu 19 displayed on the display 18. For example, if such a transit point zone is selected in the form where the characteristic image C2 shown in FIG. 17 is being displayed or is to be displayed, a pair of arrows indicating the designated zone of the transit point will be displayed on characteristic image C2, as shown in FIG. 23(*a*). Then, as shown in FIG. 23(*b*), what is displayed on the display 18 is the drawing locus reproduction image (moving image) or the still image G that dynamically displays the drawing locus drawn by the test subject in the zone of the selected transit point.

According to such a display form, a user such as a doctor who evaluates the test result can cut out a part of the drawing locus as necessary and confirm it as a still image or a moving image (preferably as an enlarged display screen). For example, by reproducing and displaying the drawing portion of interest, it becomes possible to extract an abnormal drawing trend without omission and use it for cognitive function evaluation.

Figure 16:
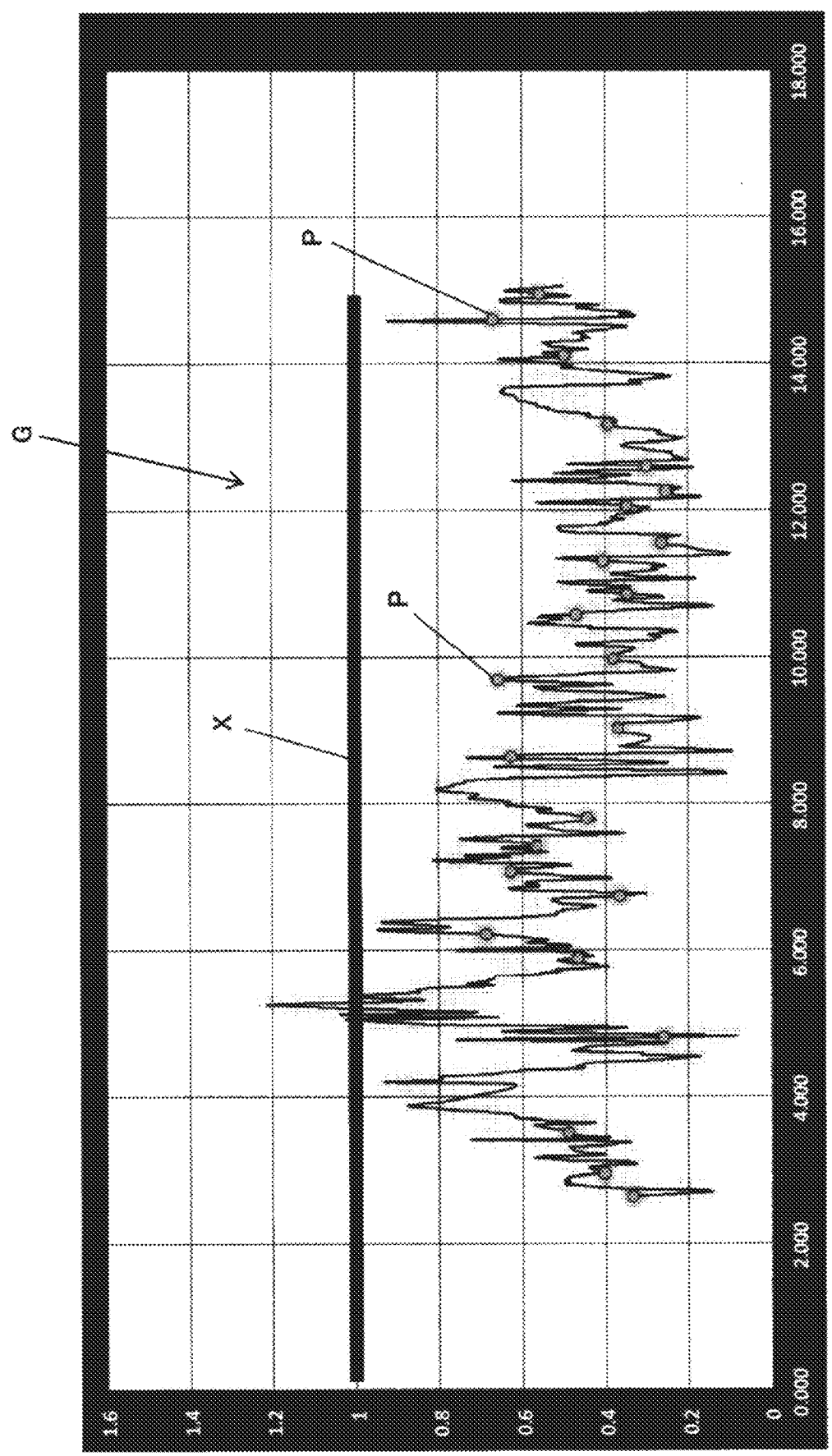
FIG. 16 shows an example of a processed image displayed as a test result on a display (a contact pressure image displaying a time-dependent change in contact pressure of a contact part with respect to a display surface of a TMT test image in association with a position of a transit point).

Further, in the terminal 1 of the present embodiment, as described above, the sensor 14 can detect a contact pressure of the contact part 80 with respect to the display surface of the TMT test image I (The pen pressure exerted on the display surface of the TMT test image I through the contact part 80 when the test subject draws a drawing locus). Accordingly, the contact pressure data acquisition circuit 46 of the test data acquisition circuit 40 can acquire contact pressure data according to the position of the contact part 80 on the coordinate surface, in accordance with the detection signal from the sensor 14 (contact pressure data acquisition step). The image generation circuit 54 can generate a contact pressure image as a processed image, which displays a change in contact pressure over time in association with the position of transit point P. FIG. 16 shows an example of such a contact pressure image G. This contact pressure image G shows a time-dependent change of the contact pressure in association with the position of transit point P. In the contact pressure image G, the horizontal axis shows time and the vertical axis shows the contact pressure. Further, in the contact pressure image G, each transit point (numbers 1 to 25) P is displayed as a dot having a predetermined size on the contact pressure-time graph.

In this way, if the contact pressure that can be an index for cognitive function evaluation can be detected and the contact pressure image G related to the contact pressure can be generated and outputted, it becomes possible to provide a useful display form that helps the cognitive function evaluation. It is known that if the cognitive function is impaired, the pen pressure may not be well controlled. Therefore, such a contact pressure image G can be very useful for cognitive function evaluation. It is preferable that the above-mentioned visually identifiable display form can be applied to such a contact pressure image G as well.

Further, in the terminal 1 of the present embodiment, the image generation circuit 54 (image generation step) can display, on the processed image, a visual index indicating a threshold value as an evaluation standard of the TMT test result. In this case, as threshold value that serves as the evaluation standard for the TMT test result, it is possible to enumerate, for example, a value that can be a boundary value between good and bad of the test result. It may be, for example, a moving speed value, an acceleration value, a jerk value, and the passing time through transit points for the contact part 80, a time required between transit points, and a contact pressure of the contact part 80 with respect to the display surface of the TMT test image I. Further, as a visual index displayed on the processed image, it is possible to enumerate lines, dots, patterns, and the like. For example, the contact pressure image G shown in FIG. 16, 1 is adopted as the threshold value of the contact pressure which is the evaluation standard of the TMT test result, and the line X indicating this threshold value is displayed as a visual index. If such an index is displayed, it is possible to grasp the quality of the test result at a glance which can be useful for rapid cognitive function evaluation. On the other hand, it is preferable that such a threshold value, which is an evaluation standard of the TMT test result, can be set to an arbitrary value from the mode selection menu 19 or the like, in accordance with the accumulated past medical data or the like. Further, it is preferable that the evaluation standard of the TMT test result can be set (for example, selection of a processed image in which the index should be displayed) from the mode selection menu 19 or the like.

The processed image including the characteristic image as described above, and the test data including the coordinate data and the time data acquired by the test data acquisition circuit 40 are stored in the memory 20. If the test data or the like can be stored in the memory 20 in this way, the data can be stored in the memory and the necessary data can be read out in a timely manner as needed. Further, for example, it is possible to evaluate the course of symptoms by comparing the accumulated historical data with each other, or to make a final certification of the evaluation in accordance with the data accumulated in the memory.

Figure 11:
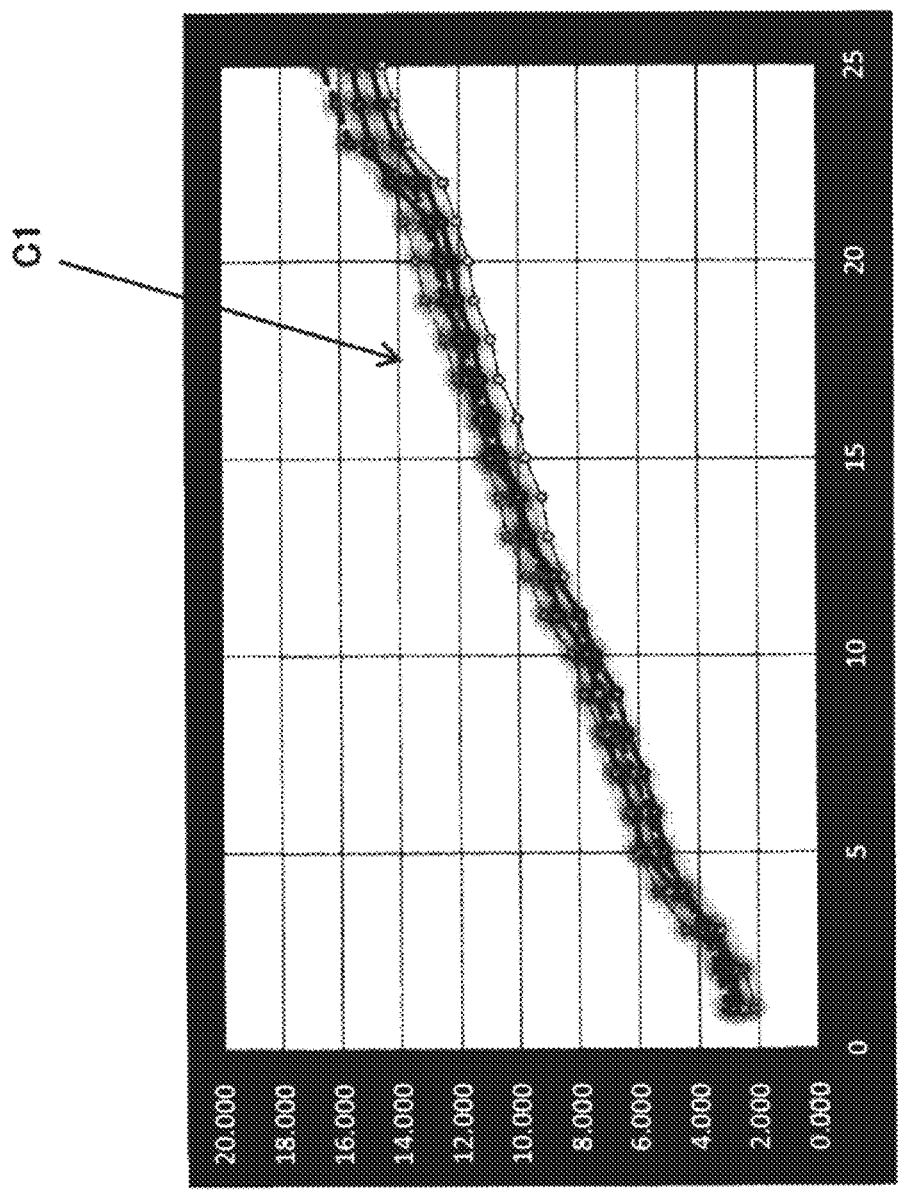
FIG. 11 shows an example of a display form in which the characteristic image shown in FIG. 10(b) is displayed in parallel with a plurality of similar past characteristic images.
Figure 12:
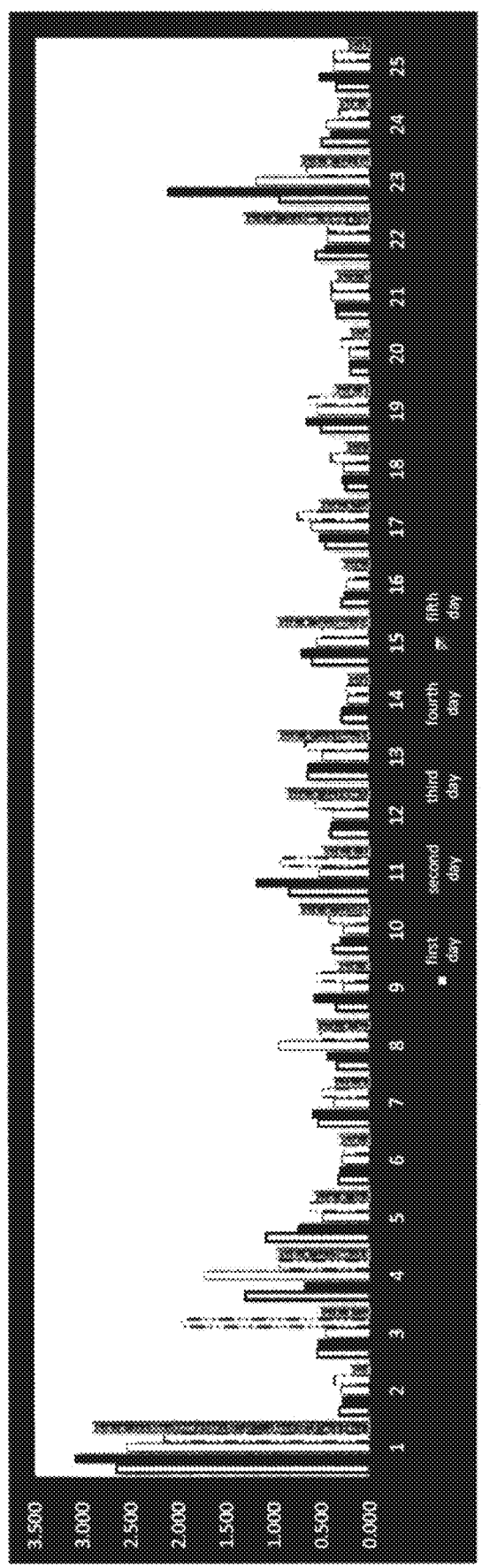
FIG. 12 is an example of a characteristic image displayed as a test result on a display (a characteristic image in which a time-dependent change of a time required by a contact part between transit points is displayed in association with a position of a transit point), showing an example of a display form in which a plurality of similar past characteristic images are displayed in parallel.

Further, due to the existence of the memory 20, the image output circuit 58 of the data processing circuit 50 can output a processed image stored in the memory 20 and determined in accordance with the input signal from the mode selection menu 19, in a display form including an alternative or parallel display determined in accordance with the input signal. For example, FIG. 11 shows a display mode in which the characteristic image C1 shown in FIG. 10(*b*) is displayed in parallel with a plurality of similar characteristic images C1 in the past. Here, the characteristic image C1 based on the past five tests including the present test (with different line types in the figure) is displayed in parallel in the above-mentioned identification display form. Further, FIG. 12 displays (in a bar graph for each transit point P) a plurality of characteristic images obtained by displaying the time required between the transit points P by the contact part 80 (in parallel for each transit point). Here, characteristic images based on five tests over a five-day period (with different patterns and line types in the figure) are displayed in parallel in the above-mentioned identification display form. Such a function of the image output circuit 58 makes it possible to customize the image display form of the test result, and in particular, by displaying the processed images in parallel. In this way, the test results can be compared and a display form useful for cognitive function evaluation can be realized. On the other hand, it should be noted that such a display function can be switched on/off via the mode selection menu 19.

Further, in addition to the above configuration, the image generation circuit 54 (image generation step) of the data processing circuit 50, uses the test data stored in the memory 20 and determined in accordance with the input signal from the mode selection menu 19, thereby generating a processed image. As a result, instead of generating only a predetermined processed image based on the predetermined test data, a desired processed image can be arbitrarily combined with the test data stored in the memory 20 by using the mode selection menu 19. For example, it is possible to display an image other than the above-mentioned characteristic image that displays a time-dependent change in the test data related to the movement of the contact part 80, in association with the position of transit point P. Specifically, it is possible to display, as a test result on the display 18, a processed image for displaying the relationship between the contact pressure and the acceleration of the contact part 80 with respect to the display surface of the TMT test image I shown in FIG. 22, in relation to the position of the transit point P. In the processed image shown in FIG. 22, the horizontal axis represents an acceleration and the vertical axis represents a contact pressure. Further, in this processed image, the data distribution is indicated by small gray dots, and each transit point (numbers 1 to 25) P is indicated by large black dots. Such a function makes it possible to customize not only the display form but also the data processing.

Further, as shown in FIG. 24 described above, the terminal 1 having the above configuration can be connected to the server 102 via the communication means (network) 100. In this case, the communication means 100 exchanges information between the terminal 1 and the server 102, and may be either wired communication or wireless communication. Examples of such a communication means 100 include a line using a wired cable, a wired telephone line, a mobile phone line, WiFi line, and the like.

Moreover, in such a using mode, the terminal 1 also includes a transmission circuit 12 (see FIG. 1) that enables data to be transmitted/received to/from the server 102 via the communication means 100. In this way, for example, the terminal 1 can send the test data obtained by itself to the server 102 and use it for the cognitive function evaluation on the server 102 side, while the terminal 1 can perform various functions based on the information from the server 102. On the other hand, it is also possible to change or increase various functions in accordance with the information from the server 102 (for example, the analysis function can be updated (the analysis program can be downloaded on the tablet (terminal 1)). Further, a more detailed analysis function may be provided on the server 102 side, and analysis result on the server 102 can be sent to the tablet. In addition, the database in the server 102 may store the user ID of the test subject, personal data such as the age, address, and gender of the test subject, the test date, the test result, and the like (main function). Moreover, it is preferable that the server 102 can be accessed by any medical institution. In addition, it is preferable that the database can be used as big data on dementia.

As described above, according to the terminal 1 (TMT test result display system S) of the present embodiment, a series of processes from the test execution to the test result acquisition (test result display) can be automated, so that it is not necessary for an inspector such as a doctor to measure the time (required for the test) with a stopwatch or the like, and it is not necessary to manually collect and analyze the obtained test data including the measured value. Therefore, it is possible to quickly and easily perform a series of processes from the execution of the test to the acquisition of the test result (display of the test result). In addition to the above functions, the terminal 1 of the present embodiment can acquire the time-dependent change in the position of contact part 80 on the coordinate plane (as time-series coordinate data) in accordance with the electrical detection signal by the sensor 14. Based on the detection signal from sensor 14, the elapsed time associated with the movement of the contact part 80 can be acquired as time data by the timer. Meanwhile, based on the above-mentioned data, it is required to calculate the test data related to the movement of the contact part 80, the contact pressure of the contact part 80 with respect to the display surface of the TMT test image that may be affected by the movement speed or the like, thereby making it possible to generate and output a characteristic image showing a test value's changes over time.

Therefore, it becomes possible to exactly catch various hidden information in the examination process that cannot be obtained only by using the measured values and drawing trajectories in association with manual measurement with a stopwatch and picture drawing by the test subject, thereby making it possible to use these hidden information in the cognitive function evaluation of the test subject. In addition, according to the automatic test form accompanied by such an electrical processing, since it is possible to eliminate human measurement errors and standardize the test conditions, it is possible to prevent a situation where the test result fluctuates depending on an inspector or each individual test. Thus. it is possible to improve the reliability of the test result.

Moreover, in the terminal 1 of the present embodiment, the characteristic image generated by the image generation circuit 54 displays a time-dependent change of the test value in association with the position of transit point P, so that it is possible to enable a detailed cognitive function evaluation by a doctor for each transit point zone, and it becomes possible to provide a useful display form that assists cognitive function evaluation. Further, according to such an automated TMT test result display system, the test subject can perform the test by himself/herself without an inspector and can confirm the test result on the spot.

On the other hand, the present invention is not limited to the above-described embodiment, but can be variously modified and implemented without departing from the gist thereof. For example, in the present invention, another process may be further added between the process steps described above, or the order of the steps may be partially changed. Further, apart or all of the above-mentioned embodiments may be combined within a range not deviating from the gist of the present invention, or a part of the configuration may be omitted from one of the above-discussed embodiments.

EXPLANATION OF REFERENCE NUMERALS 1 terminal
14 sensor
16 timer
18 display
19 mode selection menu
20 memory
25 test image generation circuit
30 control circuit
32 transit detection circuit
34 setting circuit
40 test data acquisition circuit
42 coordinate data acquisition circuit
44 time data acquisition circuit
46 contact pressure data acquisition circuit
50 data processing circuit
52 arithmetic circuit
54 image generation circuit
56 identification image generation circuit
58 image output circuit
80 contact part
S TMT test result display system

The invention claimed is:

1. A Trail Making Test (TMT) test result display system that enables execution of a TMT test on a display and displays test result on the display, the system comprising:
   a test image generation circuit that electronically generates a TMT test image which is displayed on the display and is formed by setting transit points at multiple positions on a coordinate plane;

a test data acquisition circuit that allows a test subject to move a contact part in contact with the display surface of the TMT test image and to trace the transit points in a predetermined order, thereby acquiring time-dependent data of a drawing trajectory drawn by the test subject;

a data processing circuit that processes data acquired by the test data acquisition circuit so that the processing result can be displayed as the test result on the display; and a control circuit that controls operations of each respective circuits, wherein the test data acquisition circuit includes: i) a coordinate data acquisition circuit which, in accordance with a detection signal from a sensor that detects a contact of the contact part with the display surface of the TMT test image, acquires the coordinate data corresponding to the position of the contact part on the coordinate plane; and ii) a time data acquisition circuit that uses a timer to acquire time data associated with the acquisition time of each coordinate data, and the data processing circuit includes: i) a arithmetic circuit that calculates a predetermined test value based on the coordinate data and the time data in the contact part; ii) an image generation circuit that generates characteristic images each of which displays, in association with the position of transit point, a time-dependent change of the test value calculated by the arithmetic circuit, the characteristic images corresponding to each respective region formed by dividing the coordinate plane into a plurality of regions; and iii) an image output circuit that outputs a processed image including the characteristic image generated by the image generation circuit.

2. The TMT test result display system according to claim 1, wherein the control circuit controls the operation of each circuit in accordance with an input signal from a mode selection menu which is displayed on the display and selects a test form of TMT test and a display form of the test result.

3. The TMT test result display system according to claim 2, wherein the image generation circuit includes an identification image generation circuit which divides the coordinate plane into the plurality of regions determined based on the input signal, and generates the characteristic images in a display form visually identifying data corresponding to each respective regions from each other.

4. The TMT test result display system according to claim 2, wherein the image generation circuit generates a drawing locus reproduction image that dynamically and/or statically displays the drawing locus drawn by the contact part, in a predetermined zone of the transit point determined based on the input signal.

5. The TMT Test result display system according to claim 2, further comprising a memory for storing the test data including the coordinate data and the time data and also for storing the processed image generated by the image generation circuit.

6. The TMT test result display system according to claim 5, wherein the image output circuit outputs the processed image stored in the memory and determined in accordance with the input signal, in a display form including an alternative or parallel display determined in accordance with the input signal.

7. The TMT test result display system according to claim 5, wherein the image generation circuit generates the processed image by using the test data stored in the memory and determined based on the input signal.

8. The TMT test result display system according to claim 1, wherein the test value includes any one of a speed, an acceleration, a jerk degree of the contact part, a passing time through transit point by the contact part, and a required time between the transit points.

9. The TMT test result display system according to claim 1, wherein:

the sensor further detects a contact pressure of the contact part with respect to the display surface of the TMT test image;

the test data acquisition circuit further includes a contact pressure data acquisition circuit that acquires the contact pressure data corresponding to the position of the contact part on the coordinate plane in accordance with the detection signal from the sensor; and the image generation circuit generates a contact pressure image as the processed image, which displays a time-dependent change of the contact pressure in association with the position of transit point.

10. The TMT test result display system according to claim 1, further comprising a transit detection circuit that detects a passing through a transit point by the contact part in accordance with the detection signal from the sensor, and the transit detection circuit includes a setting circuit for variably setting a range of a coordinate region which can determine that the contact part has passed through the transit point.

11. The TMT test result display system according to claim 1, wherein the image generation circuit displays, on the processed image, a visual index indicating a threshold value serving as an evaluation standard of the TMT test result.

12. A non-transitory computer readable medium storing programs that, when executed by a computer, cause the computer to execute a Trail Making Test (TMT) test on a display and display a test result of the TMT test on the display, and further cause the computer to carry out the following steps which includes:

a test image generation display step for electronically generating a TMT test image which is formed by setting transit points at a plurality of positions on a coordinate plane, said step also including displaying TMT test image on the display;

a test data acquisition step for acquiring time-dependent data of a drawing trajectory drawn by a test subject moving a contact part in contact with the display surface of the TMT test image and tracing the transit points in a predetermined order; and a data processing display step for processing the data acquired by the test data acquisition step and for displaying the processing result as the test result on the display, wherein the test data acquisition step includes: i) a coordinate data acquisition step for acquiring coordinate data corresponding to the position of the contact part on the coordinate plane in accordance with a detection signal from a sensor that detects the contact of the contact part with the display surface of the TMT test image; ii) time data acquisition step for acquiring time data associated with the acquisition time of each coordinate data by using a timer, and the data processing display step includes: i) a calculation step for calculating a predetermined test value based on the coordinate data and the time data in the contact part; ii) an image generation step that generates characteristic images each of which displays a time-dependent change of a test value calculated by the calculation step in association with the position of transit point, the characteristic images corresponding to each respective region formed by dividing the coordinate plane into a plurality of regions; and iii) an image output display step that outputs a processed image including the characteristic image generated by the image generation step and displays the image on the display.

13. The non-transitory computer readable medium according to claim 12, wherein, in accordance with an input signal from a mode selection menu that is displayed on the display so that the test form of the TMT test and the display form of the test result is selected, the TMT test is performed on the display and the test result thereof is displayed on the display.

14. The non-transitory computer readable medium according to claim 13, wherein the image generation step includes an identification display step that divides the coordinate plane into the plurality of regions determined based on the input signal, and generates the characteristic images in a display form in which the data corresponding to each respective region is visually distinguished from each other.

15. The non-transitory computer readable medium according to claim 13, further comprising a storing step for storing in a memory the test data including the coordinate data and the time data, as well as the processed image generated by the image generation step.

16. The non-transitory computer readable medium according to claim 15, wherein the image output display step selectively or parallelly displays on the display the processed image stored in the memory and determined based on the input signal, in a display form determined based on the input signal.

17. The non-transitory computer readable medium according to claim 15, wherein the image generation step generates the processed image using the test data stored in the memory and determined based on the input signal.

18. The non-transitory computer readable medium according to claim 12, wherein the test value includes any one of the speed, acceleration, jerk degree of the contact part, a passing time through the transit point by the contact part, and a required time between the transit points.

19. The non-transitory computer readable medium according to claim 12, wherein the image generation step is to generate, as a processed image, a drawing locus reproduction image that dynamically and/or statically displays the drawing locus drawn by the contact part, in a predetermined zone of the transit point determined based on an input signal.

20. The non-transitory computer readable medium according to claim 12, wherein
the sensor further detects a contact pressure of the contact part with respect to the display surface of the TMT test image,
the test data acquisition step further includes a contact pressure data acquisition step which, in accordance with the detection signal from the sensor, acquires the contact pressure data corresponding to the position of the contact part on the coordinate plane, and
the image generation step generates a contact pressure image as the processed image, which displays the time-dependent change of the contact pressure in association with the position of the transit point.

21. The non-transitory computer readable medium according to claim 12, further comprising a transit detection step which, in accordance with the detection signal from the sensor, detects the passing through the transit point by the contact part, while the transit detection step is a setting step for variably setting the range of a coordinate region in which the contact part is determined to have passed through the transit point.

22. The non-transitory computer readable medium according to claim 12, wherein the image generation step displays a visual index on the processed image, indicating a threshold value serving as an evaluation criterion of the TMT test result.

23. A Trail Making Test (TMT) test result display method that enables execution of a TMT test on a display and displays a test result on the display, the TMT test result display method allowing a computer to carry out the following steps which includes:
a test image generation display step for electronically generating a TMT test image which is formed by setting transit points at a plurality of positions on a coordinate plane, said step also including displaying TMT test image on the display;
a test data acquisition step for acquiring time-dependent data of a drawing trajectory drawn by a test subject moving a contact part in contact with the display surface of the TMT test image and tracing the transit points in a predetermined order; and
a data processing display step for processing the data acquired by the test data acquisition step and for displaying the processing result as the test result on the display the test data acquisition step includes: i) a coordinate data acquisition step for acquiring coordinate data corresponding to the position of the contact part on the coordinate plane in accordance with a detection signal from a sensor that detects the contact of the contact part with the display surface of the TMT test image; ii) time data acquisition step for acquiring time data associated with the acquisition time of each coordinate data by using a timer, and
the data processing display step includes: i) a calculation step for calculating a predetermined test value based on the coordinate data and the time data in the contact part; ii) an image generation step that generates characteristic images each of which displays a time-dependent change of a test value calculated by the calculation step in association with the position of transit point, the characteristic images corresponding to each respective region formed by dividing the coordinate plane into a plurality of regions; and iii) an image output display step that outputs a processed image including the characteristic image generated by the image generation step and displays the image on the display.

24. The TMT test result display method according to claim 23, wherein, in accordance with an input signal from a mode selection menu that is displayed on the display so that the test form of the TMT test and the display form of the test result is selected, the TMT test is performed on the display and the test result thereof is displayed on the display.

25. The TMT test result display method according to claim 24, wherein the image generation step includes an identification display step that divides the coordinate plane into the plurality of regions determined based on the input signal, and generates the characteristic images in a display form in which the data corresponding to each respective region is visually distinguished from each other.

26. The TMT test result display method according to claim 24, wherein the image generation step is to generate, as a processed image, a drawing locus reproduction image that dynamically and/or statically displays the drawing locus drawn by the contact part, in a predetermined zone of the transit point determined based on the input signal.

27. The TMT test result display method according to claim 24, further comprising a storing step for storing in a memory the test data including the coordinate data and the time data, as well as the processed image generated by the image generation step.

28. The TMT test result display method according to claim 27, wherein the image output display step selectively or parallelly displays on the display the processed image stored in the memory and determined based on the input signal, in a display form determined based on the input signal.

29. The TMT test result display method according to claim 27, wherein the image generation step generates the processed image using the test data stored in the memory and determined based on the input signal.

30. The TMT test result display method according to claim 23, wherein the test value includes any one of the speed, acceleration, jerk degree of the contact part, a passing time through the transit point by the contact part, and a required time between the transit points.

31. The TMT test result display method according to claim 23, wherein
the sensor further detects a contact pressure of the contact part with respect to the display surface of the TMT test image,
the test data acquisition step further includes a contact pressure data acquisition step which, in accordance with the detection signal from the sensor, acquires the contact pressure data corresponding to the position of the contact part on the coordinate plane, and
the image generation step generates a contact pressure image as the processed image, which displays the time-dependent change of the contact pressure in association with the position of the transit point.

32. The TMT test result display method according to claim 23, further comprising a transit detection step which, in accordance with the detection signal from the sensor, detects the passing through the transit point by the contact part, while the transit detection step is a setting step for variably setting the range of a coordinate region in which it can be determined that the contact part has passed through the transit point.

33. The TMT test result display method according to claim 23, wherein the image generation step displays a visual index on the processed image, indicating a threshold value serving as an evaluation criterion of the TMT test result.

* * * * *